US010513478B2

(12) United States Patent
Myers et al.

(10) Patent No.: US 10,513,478 B2
(45) Date of Patent: Dec. 24, 2019

(54) PROCESSES FOR PREPARING HALOGENATED ALKANES

(71) Applicant: BLUE CUBE IP LLC, Clayton, MO (US)

(72) Inventors: John D. Myers, Clayton, MO (US); Max M. Tirtowidjojo, Clayton, MO (US); Thomas U. Luebbe, Clayton, MO (US); Marc Sell, Clayton, MO (US)

(73) Assignee: BLUE CUBE IP LLC, Clayton, MO (US)

( * ) Notice: Subject to any disclaimer, the term of this patent is extended or adjusted under 35 U.S.C. 154(b) by 0 days.

(21) Appl. No.: 16/067,700

(22) PCT Filed: Jan. 4, 2017

(86) PCT No.: PCT/US2017/012223
§ 371 (c)(1),
(2) Date: Jul. 2, 2018

(87) PCT Pub. No.: WO2017/120264
PCT Pub. Date: Jul. 13, 2017

(65) Prior Publication Data
US 2019/0023631 A1 Jan. 24, 2019

Related U.S. Application Data

(60) Provisional application No. 62/277,400, filed on Jan. 11, 2016, provisional application No. 62/274,601, filed on Jan. 4, 2016.

(51) Int. Cl.
C07C 17/278 (2006.01)
C07C 17/275 (2006.01)
C07C 17/383 (2006.01)
C07C 17/386 (2006.01)
C07C 17/38 (2006.01)
C07C 17/389 (2006.01)

(52) U.S. Cl.
CPC .......... C07C 17/275 (2013.01); C07C 17/278 (2013.01); C07C 17/38 (2013.01); C07C 17/383 (2013.01); C07C 17/386 (2013.01); C07C 17/389 (2013.01); Y02P 20/582 (2015.11)

(58) Field of Classification Search
CPC .................................................. C07C 17/278
See application file for complete search history.

(56) References Cited

U.S. PATENT DOCUMENTS

| 4,885,418 A | 12/1989 | Hartung et al. |
| 8,907,147 B2 | 12/2014 | Wang et al. |
| 2014/0221705 A1* | 8/2014 | Wang .................... C07C 17/275 570/220 |

FOREIGN PATENT DOCUMENTS

WO  2012166394  6/2012

* cited by examiner

Primary Examiner — Medhanit W Bahta
(74) Attorney, Agent, or Firm — Polsinelli PC

(57) ABSTRACT

The present invention provides improved processes for preparing halogenated alkanes. In particular, the processes comprise reacting an alkene, a halogenated alkene, or combinations thereof and a halogenated methane with at least one chlorine atom.

22 Claims, 16 Drawing Sheets

# PROCESSES FOR PREPARING HALOGENATED ALKANES

FIELD OF THE INVENTION

The present disclosure generally relates to processes for preparing halogenated alkanes.

BACKGROUND OF THE INVENTION

Halogenated alkanes are useful intermediates for many products including agricultural products, pharmaceuticals, cleaning solvents, solvents, gums, silicones, and refrigerants. The processes to prepare halogenated alkanes can be time consuming, moderately efficient, and lack reproducibility.

Chloropropanes especially 1,1,1,3-tetrachloropropane and 1,1,1,3,3-pentachloropropane, are useful intermediates for many products especially for refrigerants. A general process for their preparation consists of reacting an alkene, carbon tetrachloride, a trialkylphosphate, and an iron catalyst. U.S. Pat. No. 4,650,914 teaches such a process where the process is conducted in batch mode, using a non-powder form of an iron and mechanical stirring. U.S. Pat. Nos. 6,313,360 and 8,907,147 disclose a continuous process using powdered iron and mechanical stirring. In each of these cases, these processes can be moderately efficient yet lack reproducibility and consistent yields. Developing a process which can prepare halogenated alkanes, and chlorinated propanes where the process would exhibit high reproducible, consistent higher yields, utilizes various recycling strategies, and greater through-put would be advantageous.

SUMMARY OF THE INVENTION

Provided herein are processes for preparing and isolating halogenated alkanes via the reaction between an alkene, a halogenated alkene, or combinations thereof and a halogenated methane comprising at least one chlorine atom. The process comprising: a. forming a reaction mixture in a reactor by contacting: a liquid phase comprising a halogenated methane comprising at least one chlorine atom, at least one phosphorus containing compound comprising a trialkylphosphate, a trialkylphosphite, or combinations thereof; and at least one catalyst comprising a metal, metal salt, or combinations thereof; an alkene, halogenated alkene, or combinations thereof; wherein the alkene, halogenated alkene, or combinations thereof and is at least partially absorbed into the liquid phase; b. stirring the reaction mixture; c. heating the reaction mixture; and d. producing halogenated alkanes and heavy by-products; wherein there is a gas phase above the reaction mixture. One skilled in the art would appreciate that stirring the reaction mixture and heating the reaction mixture may occur one before the other or at the same time. This is true throughout this application. The process further comprises at least one of the following process steps: (I) stirring the reaction mixture comprises jet mixing; (II) the process further comprises step e, wherein step e comprises: i. transferring at least part of the reactor contents into a first separator where two product streams (a) and (b) are formed: wherein product stream (a) comprises the halogenated alkane, halogenated methane comprising at least one chlorine atom, and an alkene or halogenated alkene; wherein product stream (b) comprises the heavy by-products, the at least one phosphorous containing compound, and at least one catalyst; ii. contacting at least a portion of product stream (b) with an ion exchange resin to form product stream (c) wherein product stream (c) contains less of at least one metal ion when compared to product stream (b); and iii. returning at least a portion of product stream (c) to the reactor; and (III) the process further comprises step f, wherein step f comprises: i. transferring at least part of the reactor contents into a first separator where two product streams (a) and (b) are formed, wherein product stream (a) comprises the halogenated alkane, halogenated methane with at least one chlorine atom, and the alkene, halogenated alkene, or combinations thereof and product stream (b) comprises the heavy by-products, the at least one phosphorous containing compound, and the at least one catalyst; ii. transferring at least a portion of product stream (b) back into the reactor; iii. transferring product stream (a) into a second separator and producing two product streams (d) and (e), wherein product stream (d) comprises the halogenated alkane and product stream (e) comprises halogenated methane with at least one chlorine atom and the alkene, halogenated alkene, or combinations thereof; and iv. optionally introducing at least a portion of product stream (e) into the reactor; wherein at least one of the first separator and the second separator comprises a reboiler, bottom stage, or both; wherein the first separator or the second separator may be separate or contained in a single separation device; wherein when the first and second separation devices are contained in a single separation device, the single separation device will separate at least a portion of product stream (d) from product streams (b) and (e); and wherein one or more of the separators is a multistage distillation column in which one or more of a gas or low boiling liquid comprising alkanes, alkenes, halogenated alkanes, halogenated alkenes, or nitrogen is introduced into first separator reboiler, second separator reboiler, first separator bottom stage, second separator bottom stage, or combinations thereof.

Other features and iterations of the invention are described in more detail below.

DETAILED DESCRIPTION OF THE INVENTION

Figure 1:
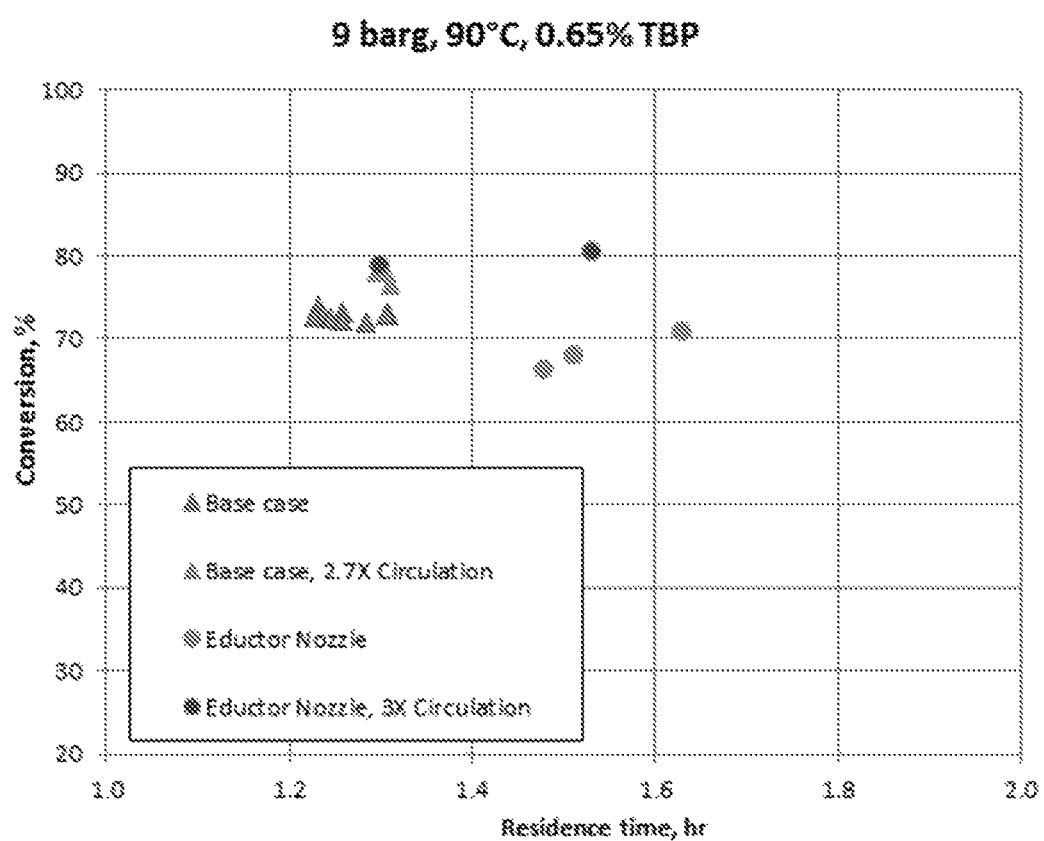
FIG. 1 shows conversion of Tet versus reactor residence time in a continuous reactor with liquid circulation through a jet nozzle (base case) and a gas eductingnozzle, each installed at the top of the reactor and aimed downward for two levels of circulation flow. Higher circulation flow is shown as a factor of the base case.

Disclosed herein are processes for the preparation of halogenated alkanes. In general, the process comprises a reaction between an alkene, halogenated alkene, or combinations thereof and halogenated methane comprising at least one chlorine atom under conditions detailed below.

In a preferred embodiment, the reaction mixture is stirred by jet mixing using at least one eductor nozzle wherein the flow from the eductor nozzle is directed towards the liquid phase of the reaction mixture is utilized.

In another preferred embodiment, the reaction mixture is separated into two product streams. Product stream (a) comprises the halogenated alkane, halogenated methane comprising at least one chlorine atom, and an alkene or halogenated alkene is separated from product stream (b) which comprises the heavy by-products, the at least one phosphorous containing compound, and at least one catalyst.

Product stream (b) may contact an ion exchange catalyst producing product steam (c). This ion exchange catalyst may remove deactivated iron catalyst, metal ions, and other impurities produced in the above process wherein product stream (c) may be returned to the process providing increased kinetics and greater cost efficiencies for the process.

In yet another preferred embodiment, a low boiling point liquid may be injected into the separators in order to facilitate effective separation at lower temperature, thereby minimizing side reactions, or higher pressure, thereby reducing capital cost and/or energy for vacuum equipment.

In an additional preferred embodiment, the reaction mixture is stirred by jet mixing using at least one eductor nozzle wherein the flow from the eductor nozzle is directed towards the liquid phase of the reaction mixture is utilized and the reaction mixture is separated into two product streams. Product stream (a) comprises the halogenated alkane, halogenated methane comprising at least one chlorine atom, and an alkene or halogenated alkene is separated from product stream (b) which comprises the heavy by-products, the at least one phosphorous containing compound, and at least one catalyst. Product stream (b) may contact an ion exchange catalyst producing product steam (c). This ion exchange catalyst may remove deactivated iron catalyst, metal ions, and other impurities produced in the above process wherein product stream (c) may be returned to the process providing increased kinetics and greater cost efficiencies for the process.

In still another preferred embodiment, the reaction mixture is separated into two product streams. Product stream (a) comprises the halogenated alkane, halogenated methane comprising at least one chlorine atom, and an alkene or halogenated alkene is separated from product stream (b) which comprises the heavy by-products, the at least one phosphorous containing compound, and at least one catalyst. Product stream (b) may contact an ion exchange catalyst producing product steam (c). This ion exchange catalyst may remove deactivated iron catalyst, metal ions, and other impurities produced in the above process wherein product stream (c) may be returned to the process providing increased kinetics and greater cost efficiencies for the process. Additionally, during the separation process, a low boiling point liquid may be injected into the separators in order to facilitate effective separation at lower temperature, thereby minimizing side reactions, or higher pressure, thereby reducing capital cost and/or energy for vacuum equipment.

In yet another preferred embodiment, the reaction mixture is stirred by jet mixing using at least one eductor nozzle wherein the flow from the eductor nozzle is directed towards the liquid phase of the reaction mixture is utilized and the reaction mixture is separated into two product streams. Additionally, during the separation process, a low boiling point liquid may be injected into the separators in order to facilitate effective separation at lower temperature, thereby minimizing side reactions, or higher pressure, thereby reducing capital cost and/or energy for vacuum equipment.

In still another preferred embodiment, the reaction mixture is stirred by jet mixing using at least one eductor nozzle wherein the flow from the eductor nozzle is directed towards the liquid phase of the reaction mixture is utilized and the reaction mixture is separated into two product streams. Additionally, the reaction mixture is separated into two product streams. Product stream (a) comprises the halogenated alkane, halogenated methane comprising at least one chlorine atom, and an alkene or halogenated alkene is separated from product stream (b) which comprises the heavy by-products, the at least one phosphorous containing compound, and at least one catalyst. Product stream (b) may contact an ion exchange catalyst producing product steam (c). This ion exchange catalyst may remove deactivated iron catalyst, metal ions, and other impurities produced in the above process wherein product stream (c) may be returned to the process providing increased kinetics and greater cost efficiencies for the process. In addition, during the separation process, a low boiling point liquid may be injected into the separators in order to facilitate effective separation at lower temperature, thereby minimizing side reactions, or higher pressure, thereby reducing capital cost and/or energy for vacuum equipment.

These processes have been shown to be an improvement in yield, purity, cycle time, selectivity, and through-put as compared to other conventional methods. An additional aspect of the present invention, the separated reactants are recycled back into the process to provide improved efficiency and cost reduction of the process.

(I) Process for the Preparation of Halogenated Alkanes

One aspect of the present disclosure encompasses processes for the preparation of halogenated alkanes. The processes comprise forming a reaction mixture comprising a halogenated methane comprising at least one chlorine atom, an alkene, halogenated alkene, or combinations thereof, and at least one phosphorus containing compound comprising a trialkylphosphite, trialkylphosphate, and combinations thereof, and at least one catalyst. Once this reaction mixture is formed, the reaction mixture is stirred and heated producing halogenated alkanes and heavy by-products are formed.

(a) Reaction Mixture

The processes commence by preparing a reaction mixture comprising a halogenated methane comprising at least one chlorine atom, an alkene, halogenated alkene, or combinations thereof, a phosphorus containing compound, and at least one catalyst.

(i) Alkene, Halogenated Alkene, or Combinations Thereof

A wide variety of alkenes, halogenated alkenes, or combinations thereof may be used in the process. As appreciated by the skilled artisan, the alkene, halogenated alkene, or combinations thereof may be introduced in the reaction as a liquid or a gas wherein the alkene, halogenated alkene, or combinations thereof may be at least partially soluble in the liquid phase. In various embodiments, the alkene, halogenated alkene, or combinations thereof may be introduced above the surface of the liquid phase or below the surface of the liquid phase through a port in the reactor. Under conditions of the process as detailed below, the alkene, halogenated alkene, or combinations thereof may be liquid and then may undergo a phase transition from a liquid to a gas. As appreciated by the skill artisan, the alkene, a halogenated alkene, or combinations thereof may be introduced into the reactor to maintain the pressure with the reactor.

Generally, the alkene, halogenated alkene, or combinations thereof comprise between 1 and 5 carbon atoms. Non-limiting examples of alkenes may be ethylene, propylene, 1-butene, 2-butene, isobutene, 1-pentene, 2-pentene, 3-pentene, 2-methyl-2-butene, 2-methyl-1-butene, and 3-methyl-1-butene. Non-limiting examples of halogenated alkenes may be vinyl chloride, vinyl bromide, vinyl fluoride, allyl chloride, allyl fluoride, 1-chloro-2-butene, 1-fluoro-2 butene, 3-chloro-1-butene, 3-fluoro-1-butene, 3-chloro-1-pentene, 3-fluoro-1-pentene, and combinations thereof. In one embodiment, the alkene is ethylene. In another embodiment, the halogenated alkene is vinyl chloride.

(ii) Halogenated Methane Comprising at Least One Chlorine Atom

A wide variety of halogenated methane comprising at least one chlorine atom may be used in this process. Non-limiting examples of halogenated methane comprising at least one chlorine atom include methyl chloride, methylene chloride, chloroform, carbon tetrachloride, chlorofluoromethane, dichloromonofluoromethane, trichlorofluoromethane, difluorochloromethane, trifluorochloromethane, bromochloromethane, dibromochloromethane, tribromochloromethane, chloroiodomethane, chlorodiiodomethane, chlorotriiodomethane, bromochlorofluoromethane, bromochlorodifluoromethane, chlorodibromofluoromethane, bromochlorofluoroiodomethane, bromochlorodiiodomethane, and combinations thereof. In an embodiment, the halogenated methane comprising at least one chlorine atom is carbon tetrachloride.

In general, the halogenated methane comprising at least one chlorine atom may be used in excess. Generally, the molar ratio of the halogenated methane comprising at least one chlorine atom to an alkene, a halogenated alkene, or combinations thereof may range from 0.1:1 to about 100:1. In various embodiments, the molar ratio of the halogenated methane comprising at least one chlorine atom to an alkene, a halogenated alkene, or combinations thereof may range from 0.1:1 to about 100:1, from 0.5:1 to about 75:1, from 1:1 to about 10:1, or from 1.2:1 to about 5:1. In various embodiments, the molar ratio of the halogenated methane comprising at least one chlorine atom to an alkene, a halogenated alkene, or combinations thereof may range from 1.2:1 to about 2:1. The halogenated methane comprising at least one chlorine atom and an alkene, a halogenated alkene, or combinations thereof are essentially dry, i.e., it has a water content of the below 1000 ppm. Lower water concentrations are preferred, but not required.

(iii) Phosphorus Containing Compound.

In various embodiments, a phosphorus containing compound may be used in the process. The phosphorus containing compound, as the skilled artisan appreciates, may form a complex with the transition metal forming a transition metal phosphorus containing compound complex which is soluble within the reaction media. Examples of phosphorus containing compound may include trialkylphosphates, trialkylphosphites, or combinations thereof. Suitable non-limiting examples of trialkylphosphates and trialkylphosphite may include triethylphosphate, tripropylphosphate, triisopropylphosphate, tributylphosphate, trimethylphosphite, triethylphosphite, tripropylphosphite, triisopropylphosphite, tributylphosphite, and tri-tertbutylphosphite. In one embodiment, the phosphorus containing compound is a trialkylphosphate, namely tributylphosphate.

(iv) Catalyst

A wide variety of catalysts may be used in the process. In some embodiments, the catalyst may be a transition metal catalyst. As used herein, the term "transition metal catalyst" refers to a transition metal element, a transition metal salt, a transition metal containing alloy, or combinations thereof. Non limiting examples of transition metals in the at least one catalyst may include iron and copper. As appreciated by the skilled artisan, the oxidation state of suitable metals may vary, and may be, for example, (0), (I), (II), and (III). Non-limiting examples of suitable transition metals may be copper (0), copper (I), copper (II), iron (0), iron (II), and iron (III). In an embodiment, the transition metal may be iron in the (0), (II), (III) oxidation states, and combinations thereof. In another embodiment, transition metal may be copper in the (0), (I), (II) oxidation states, and combinations thereof.

In some embodiments, the at least one catalyst may comprise a transition metal element. For example, the transition metal element may be in the form of a foil, a sheet, a screen, a wool, a wire, a ball, a plate, a pipe, a rod, a bar or a powder, but powders are not preferred. In other embodiments, the transition element may be part of an alloy. Non-limiting examples of alloys may be gliding metal, bronze, magnesium bronze, tin bronze, aluminum bronze, phosphor bronze, red brass, brass, cast iron, pig iron, steel, tool steel, and wootz steel. In various embodiments, the at least one catalyst may be mobilized on the surface of a support. Non-limiting examples of suitable supports may be alumina, silica, silica gel, diatomaceous earth, carbon and clay. Non-limiting examples may include copper on alumina, copper on silica, iron on carbon, iron on diatomaceous earth, and iron on clay. In an embodiment, the transition metal may be iron or copper in the form of elemental iron, elemental copper, a copper alloy, an iron alloy, or combinations thereof.

In an embodiment, the at least one catalyst may be comprise a transition metal salt. Non-limiting examples of suitable transition metal salts may include acetates, acetyacetonates, alkoxides, butyrates, carbonyls, dioxides, halides, hexonates, hydrides, mesylates, octanates, nitrates, nitrosyl halides, nitrosyl nitrates, sulfates, sulfides, sulfonates, phosphates, and combinations thereof. Non-limiting examples of suitable transition metal salts may include copper (I) chloride, copper (II) chloride, copper (I) bromide, copper (I) iodide, iron (II) chloride, iron (III) chloride, iron (II) bromide, iron (II) iodide, iron (III) bromide, copper (II) oxide, and iron (III) oxide. In an embodiment, the transition metal salt may be copper (I) chloride, copper (II) chloride, iron (II) chloride, iron (III) chloride, or combinations thereof.

In various embodiments, the iron catalyst used in the process may be in various oxidation states, such as Fe(0), Fe(II), and Fe(III). In one aspect, the iron catalyst may be Fe(0) alone as elemental iron or an iron alloy. In an additional aspect, the iron catalyst may comprise a mixture of Fe(0) and Fe(II) salt. In another aspect, the iron catalyst may comprise a mixture of Fe(0) and Fe(III) salt. In still another aspect, the iron catalyst may comprise a mixture of Fe(II) salt and Fe(III) salt. In yet another aspect, the iron catalyst may comprise a mixture of Fe(0), Fe(II) salt, and Fe(III) salt. In still another embodiment, an electrochemical cell may be utilized to adjust the ratio of Fe(II) and Fe(III) in the reaction.

In other embodiments, the copper catalyst used in the process may be in various oxidation states, such as Cu(0), Cu(I), and Cu(II). In one aspect, the copper catalyst may be Cu (0) alone as elemental copper or a copper alloy. In an additional aspect, the copper catalyst may comprise a mixture of Cu(0) and Cu(I) salt. In another aspect, the copper catalyst may comprise a mixture of Cu(0) and Cu(II) salt. In still another aspect, the copper catalyst may comprise a mixture of Cu(I) salt and Cu(II) salt. In yet another aspect, the copper catalyst may comprise a mixture of Cu(0), Cu(I) salt, and Cu(II) salt. In still another embodiment, an electrochemical cell may be utilized to adjust the ratio of Cu(I) and Cu(II) in the reaction.

Generally, the molar ratio of the at least one catalyst to halogenated methane comprising at least one chlorine atom may range from about 0:1 to about 0.1:1. In various embodiments, the molar ratio of the at least one catalyst to halogenated methane comprising at least one chlorine atom may range from 0:1 to about 0.1:1, from 0.0001:1 to about 0.05:1, from 0.0025:1 to about 0.01:1, or from 0.005:1 to about 0.008:1. In a preferred embodiment, molar ratio of the at least one catalyst to halogenated methane comprising at least one chlorine atom may range from about 0.001:1 to about 0.007:1.

In general, the molar ratio of the dissolved elemental metal to the phosphorus containing compound may range from 1:1 to about 1:1000. In various embodiments, the molar ratio of the dissolved elemental metal to the phosphorus containing compound may range from 1:1 to about 1:1000, from 1:1 to about 1:500, from 1:1 to about 1:100, or from 1:1 to about 1:10. In one preferred embodiment, the molar ratio of the dissolved elemental metal to the phosphorus containing compound may range from 1:1.5 to about 1:3.

Generally, the molar ratio of the metal salt to the phosphorus containing compound may range from 1:1 to about 1:1000. In various embodiments, the molar ratio of the metal salt to the phosphorus containing compound may range from 1:1 to about 1:1000, from 1:1 to about 1:500, from 1:1 to about 1:100, or from 1:1 to about 1:10. In one preferred embodiment, the molar ratio of the metal salt to the phosphorus containing compound may range from 1:1.5 to about 1:3.

In another embodiment, the at least one catalyst in a continuous reactor may be part of a fixed catalyst bed. In still another embodiment, the at least one catalyst in a continuous reactor may be part of a cartridge. In still another embodiment, the at least one catalyst may be part of a structured or un-structured packing where the metal is a part of the packing or un-structured packing. Using a fixed bed, a cartridge, structured packing, or unstructured packing, the catalyst may be contained and easily replaced.

In one embodiment, the ratio of the surface area of the catalyst to the halogenated methane comprising at least one chlorine atom is at least $0.1 \text{ cm}^2/(\text{g/hr})$. In another embodiment, the ratio of the surface area of the catalyst to the halogenated methane comprising at least one chlorine atom is at least $2.0 \text{ cm}^2/(\text{g/hr})$.

(v) Optional Free Radical Initiator

In other embodiments, a free radical initiator may optionally be utilized in the process. Generally, the free radical initiator may be an organic or inorganic free radical initiator. Non-limiting examples of suitable organic or inorganic free radical initiators may include azobisisobutyronitrile, di-tert-butylperoxide, tert-butyl peracetate, tert-butyl peroxide, methyl ethyl ketone peroxide, acetone peroxide, cyclohexane peroxide, 2,4-pentanedione peroxide, potassium persulfate, or combinations thereof.

In general, the molar ratio of organic or inorganic free radical catalyst to halogenated methane comprising at least one chlorine atom may range from about 1:10 to about 1:100000. In various embodiments, the molar ratio of organic or inorganic free radical catalyst to halogenated methane comprising at least one chlorine atom may range from 1:10 to about 1:100000, from 1:100 to about 1:10000, from 1:500 to about 1:5000, or from about 1:750 to about 1:1000.

(vi) Optional Use of UV or Visible Light

In various embodiments, UV or visible light may be used to enhance the reaction. In general, the exposure of UV or visible light to the reaction may occur for a period of a few minutes or throughout the entire process.

(vii) Introduction of the Catalyst(s) into the Process

Generally, the at least one catalyst may be introduced to the process in various ways. In one aspect, the at least one catalyst comprising a metal, a metal salt(s), or combinations thereof may be introduced directly into the process. In another aspect, a catalyst solution comprising at least one catalyst may be prepared by dissolving at least a portion of the metal, metal salt(s), or combinations thereof in a mixture of halogenated methane comprising at least one chlorine atom and the phosphorus containing compound, then adding this solution to the reactor. In yet another embodiment, a catalyst solution may be generated inside the reactor by mixing the metal, metal salt(s), or combinations thereof, the phosphorus containing compound, and halogenated methane comprising at least one chlorine atom. As appreciated by the skilled artisan, other methods for introducing the at least one catalyst or solution of the at least one catalyst into the reactor may be envisioned. The alkene may be in the reactor before the catalyst is added, or the alkene may be added to the reactor after the catalyst.

(b) Reaction Conditions

As appreciated by the skilled artisan, the above process may be run in a batch mode or a continuous mode, with continuous mode preferred.

In a continuous mode, a stirred tank reactor may be used, or a series of stirred tank reactor to approach the performance of an ideal plug flow reactors may be utilized to improve the overall efficiency of the process. In another embodiment, the process in continuous modes may be stirred in various methods to improve the mixing of the gas-liquid-solid system as appreciated by the skilled artisan.

In general, the process for the preparation of halogenated alkanes will be conducted to maintain the temperature from about 80° C. to about 140° C. using an internal or external heat exchanger. As appreciated by the skilled artisan, the temperature of the reactor is partially maintained by boiling off or vaporizing a portion of the reactants and products. In various embodiments, the temperature of the reaction may be maintained from about 80° C. to about 140° C., from 85° C. to about 130° C., from 90° C. to about 120° C., or from about 95° C. to about 115° C.

Generally, the process may be conducted at a pressure of about atmospheric pressure (~14.7 psi) to about 200 psi so the amount of the gases and liquid are in suitable quantities so the reaction may proceed and maintain the kinetics of the process. In various embodiments, the pressure of the process may be from about atmospheric pressure (~14.7 psi) to about 200 psi, from about 20 psi to about 180 psi, from about 40 psi to about 160 psi, from about 80 psi to about 140 psi, or from 100 psi to about 120 psi.

Generally, the reaction is allowed to proceed for a sufficient period of time until the reaction is complete, as determined by any method known to one skilled in the art, such as chromatography (e.g., GC-gas chromatography). The duration of the reaction may range from about 5 minutes to about 16 hours. In some embodiments, the duration of the reaction may range from about 5 minutes to about 16 hours, from about 1 hour to about 12 hours, from about 2 hours to about 10 hours, from about 4 hours to about 8 hours, or from about 5 hours to about 7 hours.

(c) Stirring the Reaction

As appreciated by the skilled artisan, there are many methods to stir the contents of a reactor and/or provide increased gas absorption into the liquid phase. These methods would provide increased kinetics of the process. In various embodiments, these methods simply mix the liquid phase of the reaction mixture. In other embodiments, the method not only mixes the liquid phase of the reaction mixture but also provide increased gas absorption into the liquid phase of the reaction mixture. In still another embodiment, the method provides increased absorption of the gas phase into the liquid phase of the reaction mixture of the reactor. Non-limiting methods to adequately stir the liquid phase contents of the reactor may be jet stirring, impellers, baffles in the reactor, or combinations thereof. Non-limiting examples of methods to not only mix the contents of the reactor but also provide increased gas absorption into the liquid phase of the reaction mixture may be jet stirring using at least one eductor, jet stirring comprising at least one nozzle and at least one eductor, jet stirring wherein jet stirring comprises at least one nozzle is directed through the gas phase into the liquid phase, specially designed impellers which create adequate gas absorption into the liquid phase, reactors with specially designed baffles, and combinations thereof. A non-limiting example of a method to provide increased absorption of the gas phase into the liquid phase of a reactor may be a spray nozzle wherein the liquid phase is pumped through the spray nozzle into the gas phase resulting in absorption of the gas into the liquid spray. At least one of these methods may be utilized in the process to maintain the kinetic of the process.

Jet mixing utilizing at least one nozzle, as appreciated by the skilled artisan, withdraws a portion of the liquid phase of the reaction mixture from the reactor and pumps the liquid phase back into the reactor through at least one nozzle, thereby creating turbulence in the liquid phase. The at least one nozzle may be positioned below the surface of the liquid phase, thereby creating turbulence in the liquid phase and providing increased mixing. The at least one nozzle may be positioned at the surface of the liquid phase or directed through the gas phase into the liquid phase, thereby providing increased turbulence of the reaction mixture but also provides increased absorption of the gas phase into the liquid phase.

Jet mixing utilizing at least one eductor, as appreciated by the skilled artisan, withdraws a portion of the liquid phase of the reaction mixture from the reactor and pumps the liquid phase back into the reactor through at least one gas educting nozzle. The eductor nozzle provides suction in the eductor which pulls gas from the gas phase of the reaction mixture, mixes the gas with the circulated liquid phase, and returns the resulting mixture of liquid and gas back into the liquid phase of the reactor where the liquid had increased absorption of the gas as compared to the circulated liquid phase. When the flow from the eductor nozzle is directed towards the liquid phase of the reaction mixture, increased gas absorption of the gas in the liquid phase and increased turbulence of the reaction mixture result.

Jet mixing may also utilize at least one nozzle and at least one eductor. In this configuration, as described above, not only increased turbulence in the reaction mixture but also increased gas absorption of the gas into the liquid phase may be realized.

The use of a spray nozzle may also be utilized. Using a spray nozzle, the liquid phase is pumped through the spray nozzle producing droplets of the liquid phase from the reaction mixture. These droplets may be discharged into the gas phase, where they absorb at least some of the gas phase. The droplets are then reincorporated into the liquid phase of the reaction mixture, thereby increasing the amount of gas dissolved in the liquid phase of the reaction mixture.

In other embodiments, a draft tube may be utilized in the process. The draft tube provides an internal recirculation of the reaction mixture. The circulation may be induced by energy from the at least one liquid jets, from the at least one gas educting nozzle, from rising gas bubbles within the reactor, or a combination thereof.

As appreciated by the skilled artisan, at least one of the methods or a combination of these may be utilized in the process. In a preferred embodiment, jet mixing using at least one eductor nozzle wherein the flow from the eductor nozzle is directed towards the liquid phase of the reaction mixture is utilized.

(d) Output from the Process to Prepare Halogenated Alkanes

The process, as outlined above, produces the halogenated alkanes and heavy by-products. In general, the process produces the halogenated alkanes in at least 50 weight percent (wt %) in the liquid phase of the reactor. In various embodiments, the halogenated alkane is produced in at least 50 wt %, in at least 60 wt %, in at least 70 wt %, in at least 80 wt %, in at least 90 wt %, in at least 95 wt %, or in at least 99 wt % in the liquid phase of the reactor.

Generally, the process produces halogenated alkanes and heavy by-products. These heavy by-products are produced in less than 5 weight % in the entire product distribution. In various embodiments, these heavy impurities may be less than 4 weight %, less than 3 weight %, less than 2 weight %, or less than 1 weight %.

In preferred embodiments, the halogenated alkane is a chloroalkane wherein the chloroalkane is 1,1,1,3-tetrachloropropane or 1,1,1,3,3,-pentachloropropane.

(II) Separation of the Halogenated Alkane and Recycle Streams

The next step in the process comprises separating purified halogenated alkane from the contents of the reactor comprising halogenated alkane, a halogenated methane comprising at least one chlorine atom, an alkene, halogenated alkene, or combinations thereof, the phosphorus containing compound, at least one catalyst, heavy by-products, and light impurities through at least one of the first separator and a second separators in order to isolate the halogenated alkane in the desired yield and/or purity. In various embodiments, the at least one of the first separator and the second separator may a distillation column or a multistage distillation column. Additionally, the at least one of the first separator and the second separator may further comprise a reboiler, a bottom stage, or a combination thereof. Various distillation columns may be used in this capacity. In one embodiment, a side draw column or a distillation column which provides outlet stream from an intermediate stage or a divided wall column (dividing wall column (DWC) is a single shell, fully thermally coupled distillation column capable of separating mixtures of three or more components into high purity products may be used as a separator. A portion of various product streams produced by the process may be recycled back into the reactor to provide increased kinetics, increased efficiencies, reduced overall cost of the process, increased selectivity of the desired halogenated alkane, and increased yield of the desired halogenated alkane.

The process utilizing one separator commences by transferring a portion of the contents or the contents of the reactor into the separator. In this operation, a portion of the process contents may be separated into two distinct product streams, product stream (a) and (b). Product stream (a) comprises the halogenated alkane, halogenated methane comprising at least one chlorine atom, and an alkene or halogenated alkene is separated from product stream (b) which comprises the heavy by-products, the at least one phosphorous containing compound, and at least one catalyst.

In an embodiment, a solid/liquid phase separation device may be utilized. During the heating of the process, solids are formed. Utilization of this solid/liquid separation device removes the solids and prevents fowling of the reactor.

In another embodiment, product stream (b) may undergo further processing. Product stream (b) may contact an ion exchange catalyst producing product steam (c). This ion exchange catalyst may remove deactivated iron catalyst, metal ions, and other impurities produced in the above process. The removal of these species may prevent fowling of the reactor and/or the reboiler in the purification columns but also maintains the activity of the at least one catalyst. Product steam (c) would contain less metal ions as compared to product stream (b). Product stream (c) after contacting the ion exchange catalyst may then be recycled back into the reactor. This product stream may contain useful amounts of the phosphorus containing compound, maintain the activity of the at least one catalyst, maintain the kinetics of the process, and reduce the cost of the process.

In various embodiments, the ion exchange resin may be a cation exchange resin. Non-limiting examples of cation exchange resins may be polystyrene resin containing sulfonic acid groups, a polystyrene resin containing salts of sulfonic acid groups, polystyrene/divinylbenzene resin containing sulfonic acid groups, polystyrene/divinylbenzene resin containing salts of sulfonic acid groups, polystyrene resin containing carboxylic acid groups, a polystyrene resin containing salts of carboxylic acid groups, polystyrene/divinylbenzene resin containing carboxylic acid groups, polystyrene resin containing salts of carboxylic acid groups, polystyrene/divinylbenzene resin containing salts of carboxylic acid groups, and combinations thereof; where the cation exchange resin are in the sodium or hydrogen form, and wherein metal ions in the reaction mixture are exchanged with sodium or hydrogen ions. In preferred embodiments, the cation exchange resin may be polystyrene resin containing sulfonic acid groups, a polystyrene resin containing salts of sulfonic acid groups, polystyrene/divinylbenzene resin containing sulfonic acid groups, polystyrene/divinylbenzene resin containing salts of sulfonic acid groups, and combinations thereof wherein metal ions in the reaction mixture are exchanged with sodium or hydrogen ions.

In another embodiment, a portion of product stream (a) may be transferred into a second separator, producing two additional product streams (d) and (e). Product stream (d) comprises purified halogenated alkane while product stream (e) comprises a halogenated methane comprising at least one chlorine atom and the alkene, halogenated alkene, or combinations thereof. Product stream (d) may be further transferred into additional separators to achieve the desired yield and/or purity of the halogenated alkane.

In another embodiment, the first and second separation devices may be contained in a single separation device. In this configuration, the product stream (d) comprising the halogenated alkane may be removed as a side stream, product stream (e) comprising unconverted halogenated methane with at least one chlorine atom, the alkene, halogenated alkene, or combinations thereof, and light byproducts may be removed as the overhead stream, and product stream (b) comprising the phosphorus containing compound and heavy by-products may be removed as a bottom stream. This configuration would provide additional efficiency as compared to the other configurations. Each product stream (b), (d), and/or (e) may be returned to the reactor, purified, or purged. In yet another embodiment, the first column may use a dividing wall column to improve the purification of the product. Using this configuration of a separation device, a portion of product stream (d) may be separated from product streams (b) and (e).

Either the first or second or both separators may be multistage distillation column operated above atmospheric pressure or under vacuum to facilitate separation at lower temperature, thereby reducing the tendency to undergo side reactions that could cause loss of product or equipment fouling. In one embodiment, a low boiling point liquid, comprising an alkane, an alkene, a halogenated alkene, nitrogen, halogenated alkane with at least one chlorine atom, or combinations thereof, may be injected into the separators, preferably into the first separator reboiler, the second separator reboiler, the first bottom stage, the second bottom stage, or combinations thereof, in order to facilitate effective separation at lower temperature, thereby minimizing side reactions, or higher pressure, thereby reducing capital cost and/or energy for vacuum equipment. In another embodiment, halogenated alkane with at least one chlorine atom is injected to the first distillation column which accepts the reactor content whereas the alkene, halogenated alkene, or combination thereof is injected to the second and/or the third columns. In another embodiment, the first distillation column reboiler is the reactor. In this configuration, the reactor temperature is partially maintained by boiling off or vaporizing a portion of the reactants and the products to increase through-put of the process. In still another embodiment, the pressure of the reactor may be maintained from about atmospheric pressure (~14.7 psi) to 200 psi. These conditions for the separation maintains high purity halogenated alkane while minimizing impurities.

In various embodiments, at least a portion of product streams (b) and/or (e) may be recycled back into the reactor or mixed with fresh feed before being recycled back into the reactor. These streams may also be fed into another process to produce other products. In yet another embodiment, product stream (b) may be separated so that a portion of the heavy byproducts are returned to the reactor while the remaining portion of the heavy byproducts may be purged from the reactor. These streams may also be fed into another process to produce other products. These steps may be performed in order to improve the efficiency, reduce the cost, reduce contaminants, and increase through-put of the process.

In yet another embodiment, the at least one catalyst may be separated from the product stream by means of extraction. This extraction, using water or another polar solvent, may remove spent or deactivated catalyst. In another embodiment, the extraction may separate the active transition metal phosphorus complex which may be introduced back into the reactor or other downstream processes. Using the extraction processes defined above may provide added efficiency to the process in respect to overall cost.

Product streams (c) or (d) comprising the halogenated alkane produced in the process may have a yield of at least about 20%. In various embodiments, the product streams (c) or (d) comprising halogenated alkane produced in the process may have a yield of at least about 30%, at least about 50%, at least about 70%, at least about 75%, at least about 80%, at least about 85%, at least about 90%, at least about 95%, or at least about 99%.

The halogenated alkane contained in product streams (c) or (d) from the process may have a weight percent at least about 50%, at least about 60%, at least about 65%, at least about 70%, at least about 75%, at least about 80%, at least about 85%, at least about 90%, at least about 95%, at least about 99%, at least about 99.5%, or at least about 99.9%.

In preferred embodiments, the halogenated alkane is 1,1,1,3-tetrachloropropane and 1,1,1,3,3-pentachloropropane.

(III) Preferred Embodiments: 1,1,1,3-tetrachloropropane (a) Process for the Preparation of 1,1,1,3-tetrachloropropane One aspect of the present disclosure encompasses processes for the preparation of 1,1,1,3-tetrachloropropane. The process commences by contacting ethylene, carbon tetrachloride, a phosphorus containing compound comprising trialkylphosphate, trialkylphosphite, or combinations thereof, and at least one catalyst under the reaction conditions described above.

(b) Reaction Conditions

The reaction conditions are described above in Section (I)(b).

(c) Stirring the Reaction Mixture

The stirring of the reaction mixture is described above in Section (I)(c).

(d) Output from the Process to Prepare 1.1.1.3-Tetrachloropropane

In a preferred embodiment, the process produces 1,1,1,3-tetrachloropropane and also heavy by-products with boiling point higher than that of the desired product 1113 and other impurities such as light byproducts with boiling point less than that of the desired product 1113. As appreciated by the skilled artisan, the process is conducted to minimize the formation of byproducts and maximize the formation of 1,1,1,3-tetrachloropropane. Non-limiting examples of the heavy by-products may include 1,1,1,5-tetrachloropentane and pentachloropropane isomers.

Generally, the process produces 1,1,1,3-tetrachloropropane in at least 50 wt % yield, and produces heavy by-product impurities in less than 5 weight % in the entire product distribution. In various embodiments, the 1,1,1,3-tetrachloropropane is produced in at least 50 wt %, in at least 60 wt %, in at least 70 wt %, in at least 80 wt %, in at least 90 wt %, in at least 95 wt %, or in at least 99 wt % in the liquid phase of the reactor. In other embodiments, the heavy by-products may be less than 4 weight %, less than 3 weight %, less than 2 weight %, or less than 1 weight % in the liquid phase of the reactor.

(e) Separation of 1,1,1,3-Tetrachloropropane and Recycle Streams

The separation of 1,1,1,3-tetrachloropropane and the recycle streams is described above in Section (I)(e).

Product streams (c) or (d) comprising the 1,1,1,3-tetrachloropropane produced in the process may have a yield of at least about 20%. In various embodiments, the product streams (c) or (d) comprising 1,1,1,3-tetrachloropropane produced in the process may have a yield of at least about 30%, at least about 50%, at least about 70%, at least about 75%, at least about 80%, at least about 85%, at least about 90%, at least about 95%, or at least about 99%.

The 1,1,1,3-tetrachloropropane contained in product streams (c) or (d) from the process may have a weight percent at least about 50%, at least about 60%, at least about 65%, at least about 70%, at least about 75%, at least about 80%, at least about 85%, at least about 90%, at least about 95%, at least about 99%, at least about 99.5%, or at least about 99.9%.

(IV) Process for the Preparation of 1,1,1,3,3-Pentachloropropane (a) Process for the Preparation of 1,1,1,3,3-pentachloropropane One aspect of the present disclosure encompasses processes for the preparation of 1,1,1,3,3-pentachloropropane. The process commences by contacting vinyl chloride, carbon tetrachloride, a phosphorus containing compound comprising trialkylphosphate, trialkylphosphite, or combinations thereof, and at least one catalyst, under the reaction conditions described above.

(b) Reaction Conditions

The reaction conditions are described above in Section (I)(b).

(c) Stirring the Reaction Mixture

The stirring of the reaction mixture is described above in Section (I)(c).

(d) Output from the Process to Prepare 1,1,1,3,3-Pentachloropropane

In a preferred embodiment, the process produces 1,1,1,3,3-pentachloropropane and also heavy by-products with boiling point higher than that of the desired product 11133 and other impurities such as light byproducts with boiling point less than that of the desired product 11133. As appreciated by the skilled artisan, the process is conducted to minimize the formation of byproducts and maximize the formation of 1,1,1,3,3-pentachloropropane. Non-limiting examples of the heavy by-products may include hexachloropropane isomers.

Generally, the process produces 1,1,1,3,3-pentachloropropane in at least a 50 wt % and produces heavy by-product impurities in less than 5 weight % in the entire product distribution. In various embodiments, the 1,1,1,3,3-pentachloropropane is produced in at least 50 wt %, in at least 60 wt %, in at least 70 wt %, in at least 80 wt %, in at least 90 wt %, in at least 95 wt %, or in at least 99 wt % in the liquid phase of the reactor. In other embodiments, the heavy by-products may be less than 4 weight %, less than 3 weight %, less than 2 weight %, or less than 1 weight % in the liquid phase of the reactor.

(e) Separation of 1,1,1,3,3-Pentachloropropane and Recycle Streams

The separation of 1,1,1,3,3-pentachloropropane and the recycle streams is described above in Section (I)(e).

Product streams (c) or (d) comprising the 1,1,1,3,3-pentachloropropane produced in the process may have a yield of at least about 20%. In various embodiments, the product streams (c) or (d) comprising 1,1,1,3,3-pentachloropropane produced in the process may have a yield of at least about 30%, at least about 50%, at least about 70%, at least about 75%, at least about 80%, at least about 85%, at least about 90%, at least about 95%, or at least about 99%.

The 1,1,1,3,3-pentachloropropane contained in product streams (c) or (d) from the process may have a weight percent at least about 50%, at least about 60%, at least about 65%, at least about 70%, at least about 75%, at least about 80%, at least about 85%, at least about 90%, at least about 95%, at least about 99%, at least about 99.5%, or at least about 99.9%.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The following abbreviations are used to describe various components in the examples.

M3 Chloroform
M4 Carbon Tetrachloride
PER Perchloroethylene
1113TCP 1,1,1,3-tetrachloropropane
1115TCPN or 1115TCP 1,1,1,5-tetrachloropentane
CLBA 1-chlorobutane
EDC 1,2-dichloroethane
111TCPA 1,1,1-trichloropropane
HCE Hexachloroethane
11133C3 1,1,1,3,3-pentachloropropane
11223C3 1,1,2,2,3-pentachloropropane
1117C7 1,1,1,5-tetrachloropentane
TBP Tributylphosphate Having described the invention in detail, it will be apparent that modifications and variations are possible without departing from the scope of the invention defined in the appended claims.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1: Test Production of 1,1,1,3-Tetrachloropropane in a Continuous Reactor A continuous cylindrical reactor was constructed from Monel with a volume of 7 L. The bottom section was packed with iron (Fe(0)) with surface area per unit liquid volume of 2.27 1/cm. The liquid volume in the reactor was maintained at about 3.5 liters, which was slightly above the Fe packing. The top section was equipped with various devices through which liquid drawn from the bottom of the reactor was pumped, including a liquid jet nozzle (base-case) and a gas educting nozzle. The flow of liquid circulated from the bottom to the top of the reactor was varied from about 1× to 3× the base case rate. Liquid was also circulated from the bottom of the reactor through a heat exchanger to maintain a specified temperature of 90-110° C. The Tet feed mixture was continuously pumped into the reactor and liquid product was continuously withdrawn to maintain level. The superficial residence time in the reactor based on Tet feed, not including volume in the circulation piping and equipment was 1-2 hr. Ethylene was fed to the top of the reactor at a rate sufficient to maintain a specified pressure of 5-12 bar. Samples of liquid from the reactor were collected and analyzed by gas chromatography.

Figure 2:
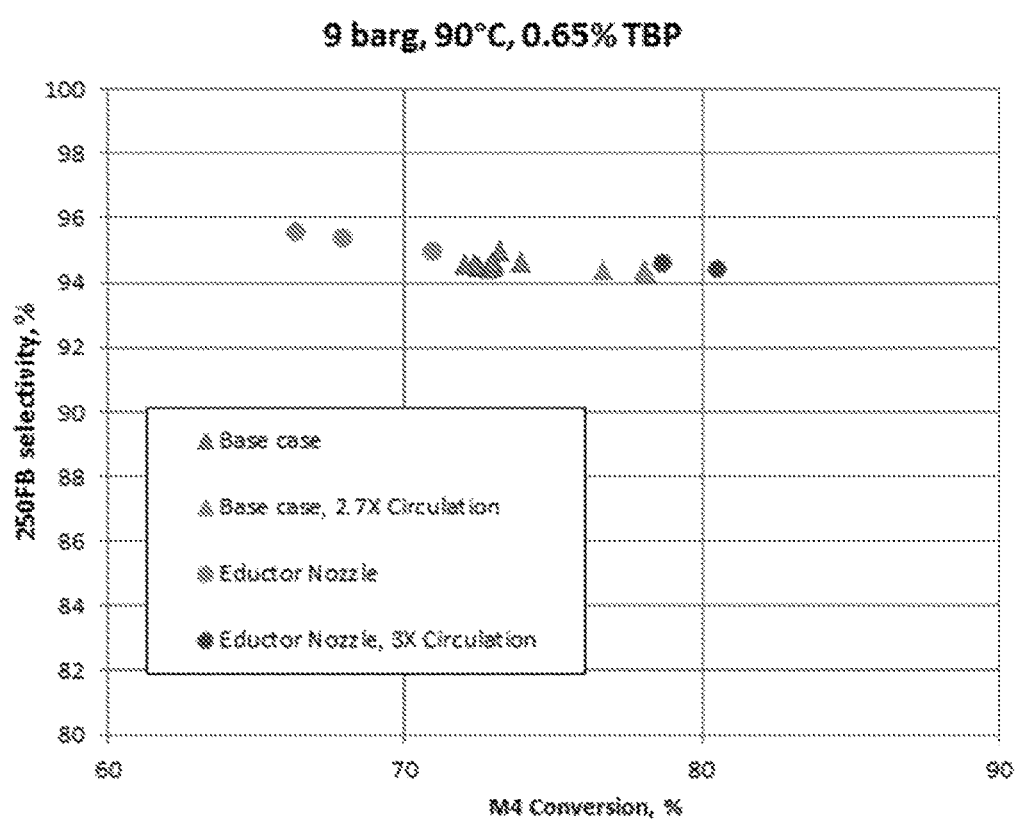
FIG. 2 presents conversion versus time data for replicate runs with two levels of iron metal surface area in a batch autoclave. Higher conversion is achieved with more metal surface area.

FIG. 1 shows M4 conversion plotted against residence time at two levels of liquid circulation rate to the top of the reactor. Two different nozzles were used to inject the circulated liquid: a jet nozzle (base case) and an eductor. Higher circulation rates resulted in faster reaction kinetics due to both improved gas/liquid and liquid/solid mass transfer characteristics. FIG. 1 also shows Tet conversion improved with higher residence time (lower M4 feed rate) and higher recirculation rate both in the base case and the eductor case at constant temperature, pressure and TBP concentration. The data labeled "base case" had a ½" ID liquid nozzle in the top of the reactor headspace directed downward into the liquid. FIG. 2 shows that the selectivity of the base case and the eductor nozzle case remained above 94% at 80% M4 conversion and higher at lower conversion.

Example 2: Test Production of 1,1,1,3-Tetrachloropropane in a Batch Autoclave

Figure 3:
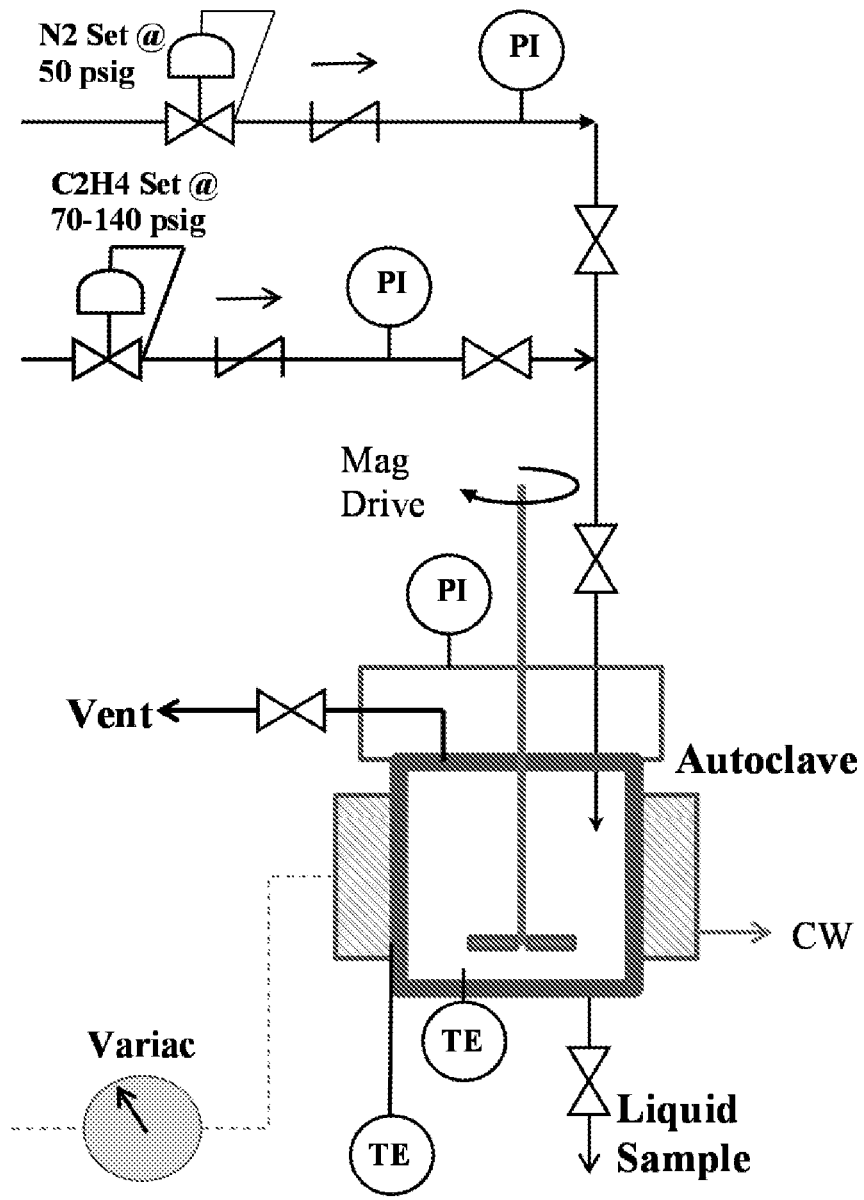
FIG. 3 presents a diagram of the lab-scale batch autoclave to test production of 1,1,1,3-tetrachloropropane (250fb).

The following protocol was designed to test production of 1,1,1,3-tetrachloropropane (250fb) in the lab by reaction of carbon tetrachloride (Tet) and ethylene in the presence of an iron catalyst (metal and/or $FeCl_3$) and an alkyl phosphate promoter in an autoclave with about 10-15 cc liquid volume. The experimental set-up is shown in FIG. 3. Reaction kinetics and selectivity were measured. Various test runs were performed in which temperature, iron surface area, $FeCl_3$ and phosphate addition, ethylene pressure, and/or stirring rate were varied. The autoclave was prepared by adding iron wire or chips to the autoclave (the wire can be coiled onto the stirring impeller or coiled in bottom of reactor). Alternatively, iron beads or other geometries can be employed to provide the necessary surface area. A stock solution of 10% $FeCl_3$, 17.5% tributylphosphate (TBP) and 72.5% carbon tetrachloride (Tet) by weight was prepared. For the baseline runs (M, R, S, T, U, W, 2A using 1.9 cm2 metal and 2B-2F, 2J, 2P using 11.5 cm2 Fe metal), 17 g Tet, 0.126 g tributylphosphate, and 0.765 g stock solution were added to a vial and mixed. The liquid reactants were poured into the reactor (autoclave), the reactor was sealed, and stirring was started. The autoclave was purged with nitrogen two times and purged with ethylene three times (with stirring to help remove some inerts and trace water from the liquid reactants.) Then, the autoclave was padded with ethylene to about 120 psig, and the ethylene feed was closed. The autoclave was heated to the desired temperature (90-120° C.). When the desired temperature was reached, the ethylene feed valve was opened and the pressure was set to the desired level. Samples (0.3 cc) were removed at regular intervals (e.g., 1, 2, 3 hours) and analyzed by GC. When the reaction was complete (or desired Tet conversion achieved), the heat was turned off, the system was cooled to below 35° C., the ethylene was turned off, and the system was vented. The final weight of the iron wire was measured. Table 1 presents the reaction conditions for the test runs. Runs were conducted at 90-120° C., 60-140 psig, and 150-1100 rpm stirring rate. The amounts of iron metal, iron chloride and TBP were varied. Table 2 presents some reaction parameters for the test runs and Table 3 presents the conversion and selectivity data.

Figure 4:
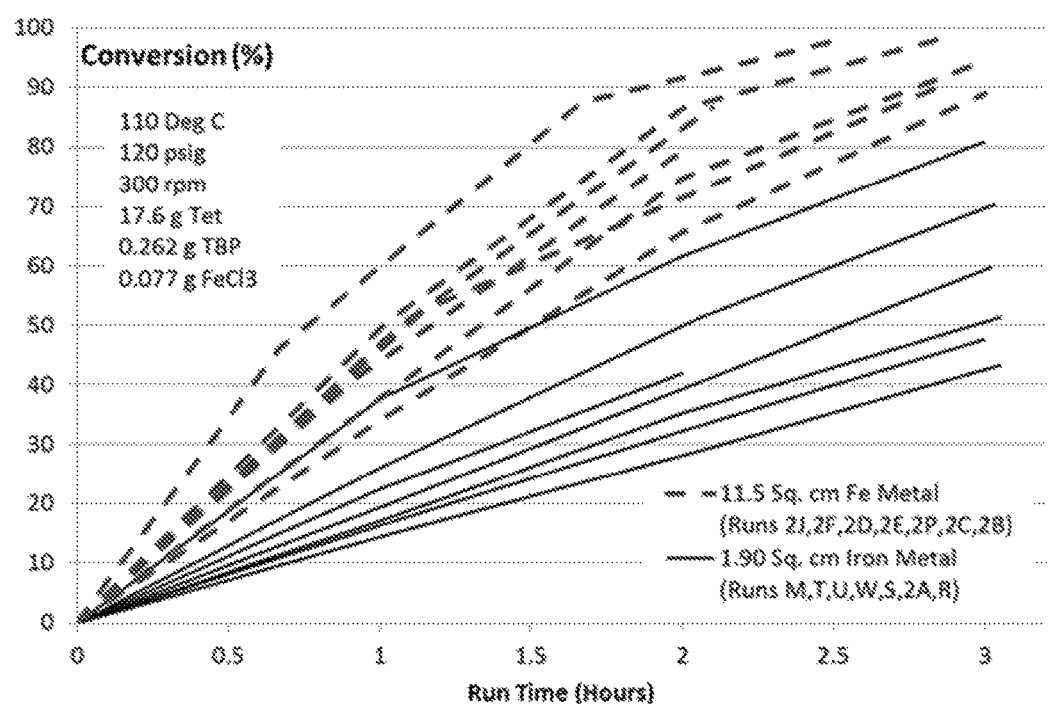
FIG. 4 presents conversion versus time data for replicate runs with two levels of iron metal surface area in a batch autoclave. Higher conversion is achieved with more metal surface area.
Figure 5:
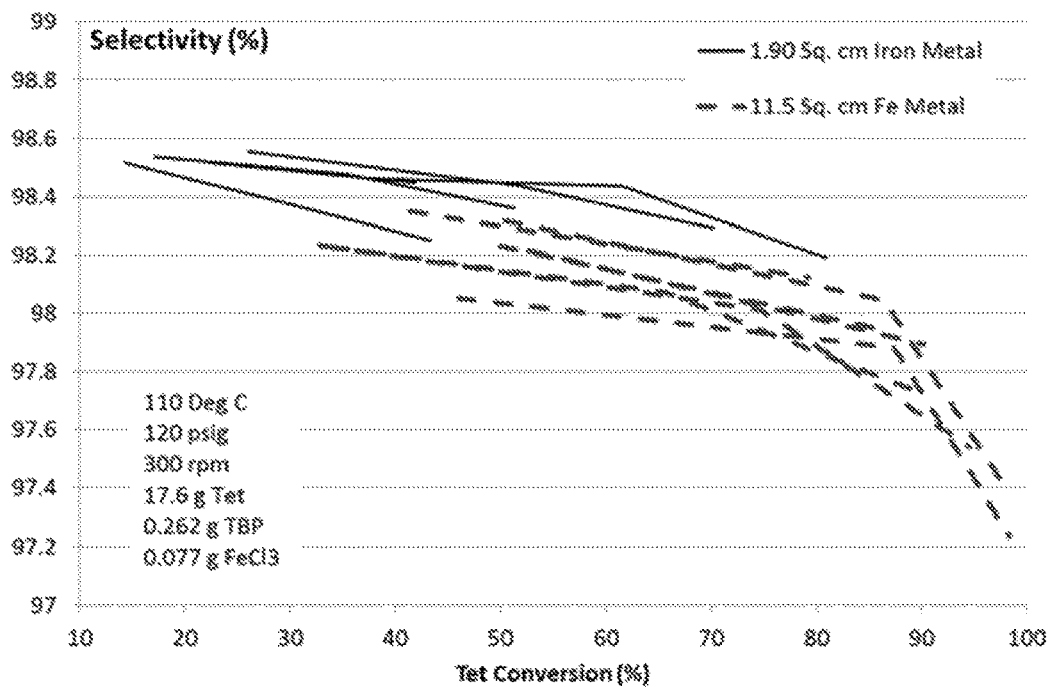
FIG. 5 Presents selectivity versus conversion data for replicate runs with two levels of iron metal surface area in a batch autoclave. Slightly higher selectivity was achieved with less metal surface.
Figure 6:
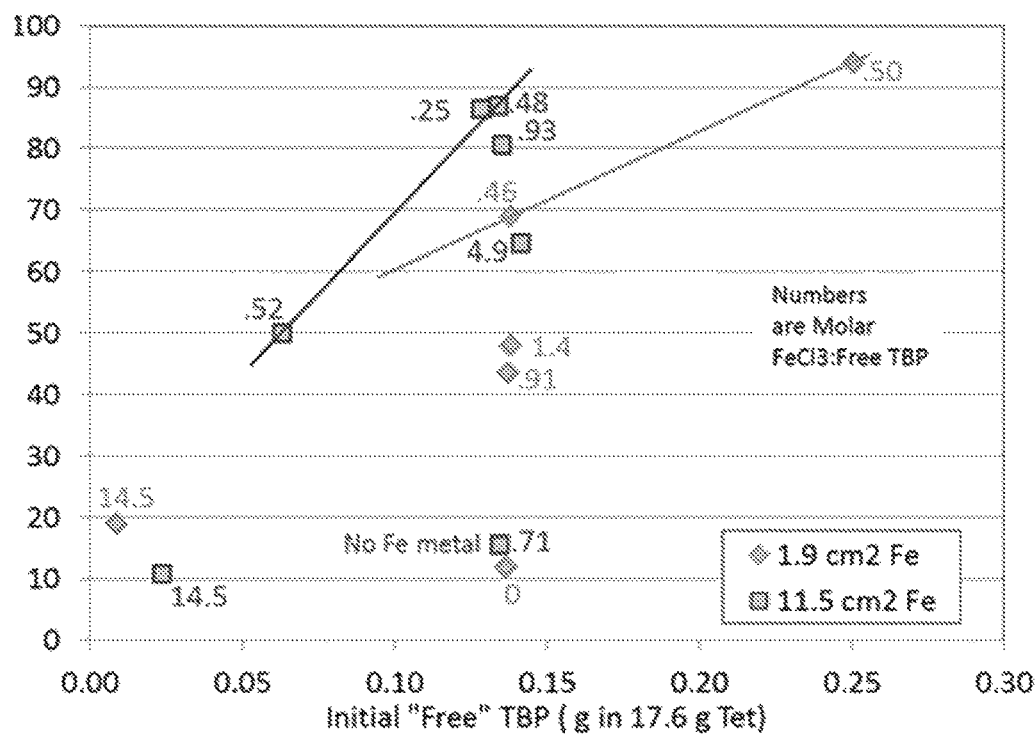
FIG. 6 presents Tet conversion at 2 hours run time with varying Iron and TBP concentrations in a batch autoclave, demonstrating that free (in molar excess of dissolved iron) TBP improves kinetics. Kinetics are very slow with no iron metal or no added iron chloride. At comparable free TBP levels, high iron chloride addition at the start of a run (high FeCl3: free TBP molar ratio) resulted in slower kinetics.
Figure 7:
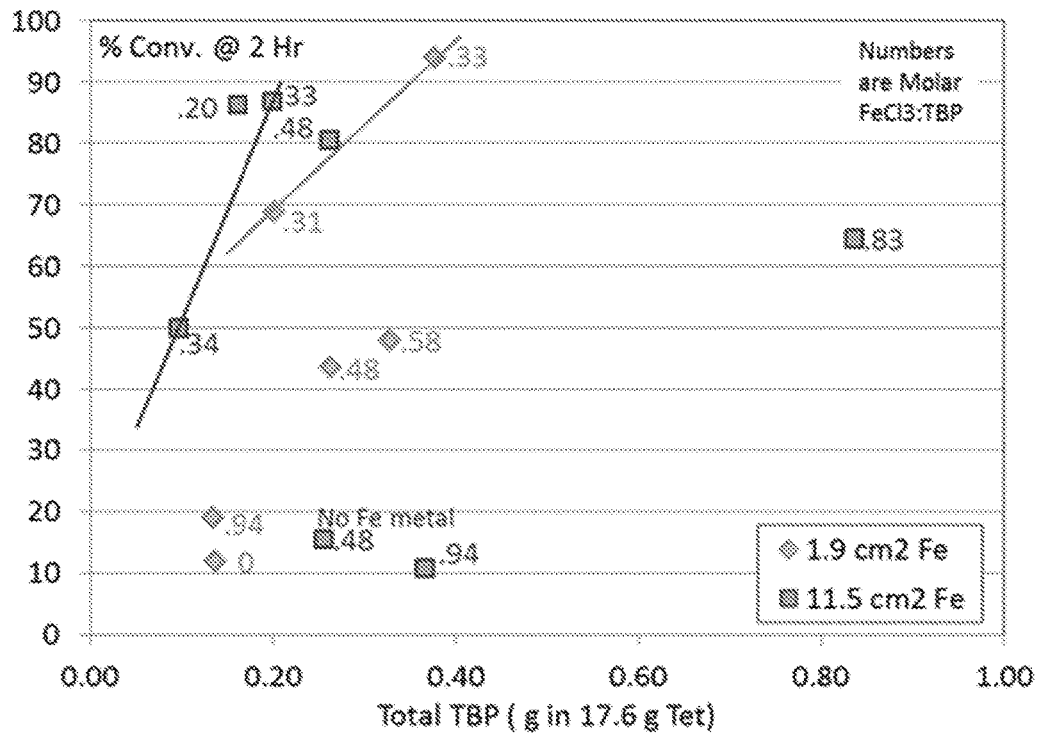
FIG. 7 presents the data of FIG. 4 plotted against total TBP concentration, demonstrating that TBP that is complexed with iron does not contribute to higher conversion.
Figure 8:
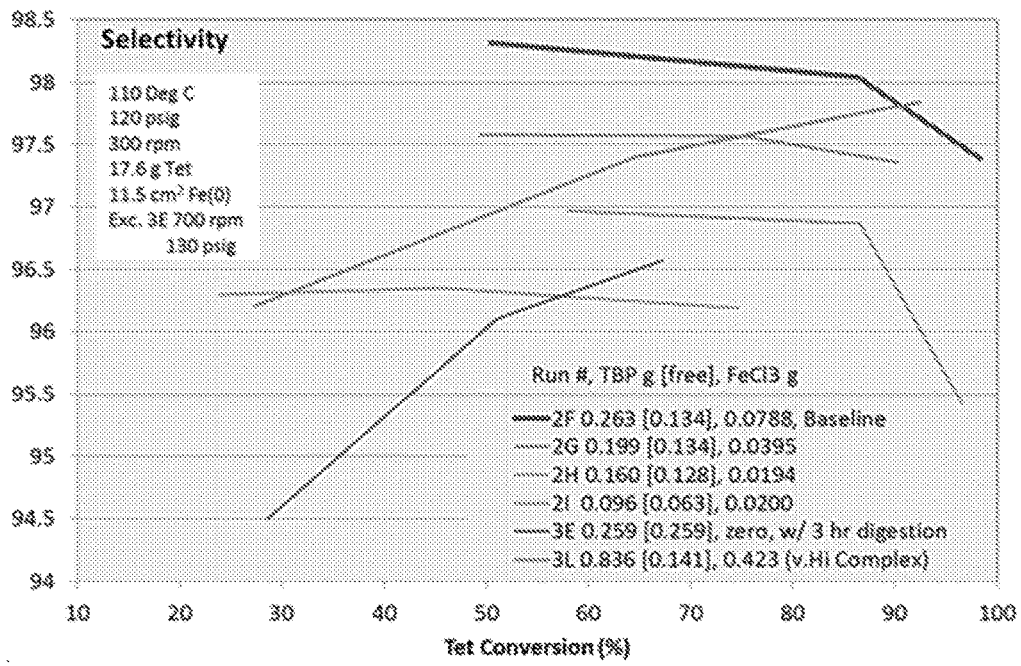
FIG. 8 presents selectivity to 250fb data versus conversion for varying catalyst and TBP concentrations. Generally, higher Fe-TBP complex and higher free TBP both contribute to higher selectivity.
Figure 9:
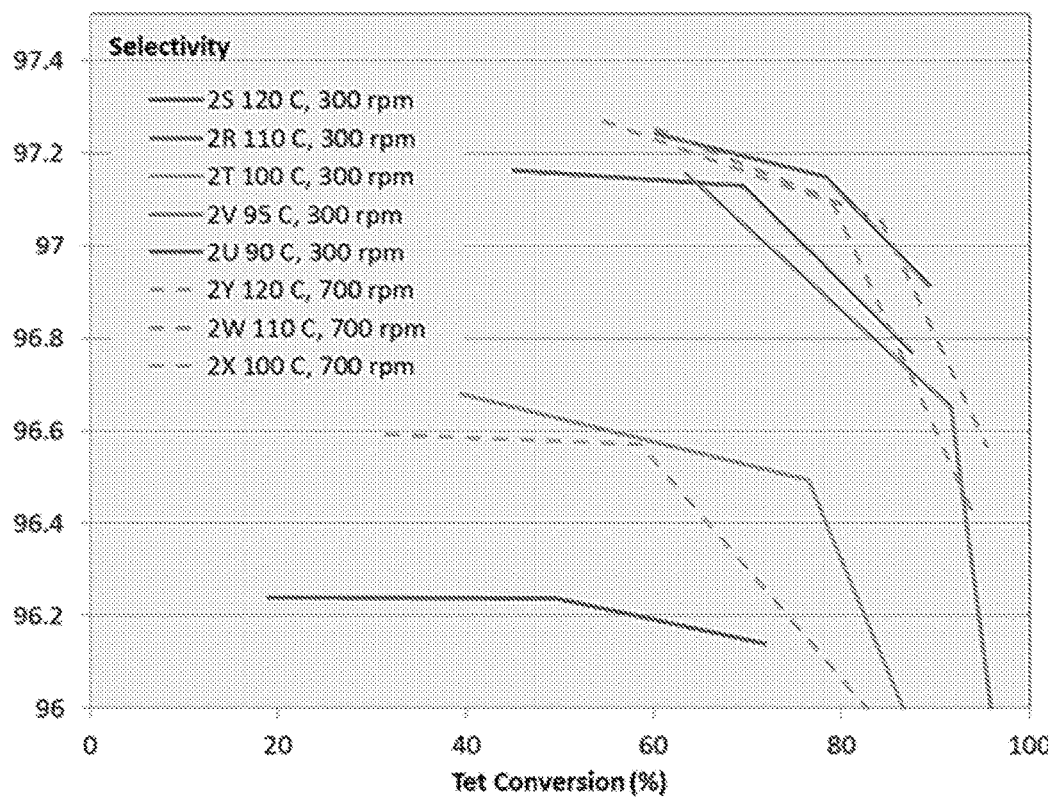
FIG. 9 presents selectivity to 250fb data versus conversion for varying temperature and stirring rate. Generally, higher temperature resulted in higher selectivity.
Figure 10:
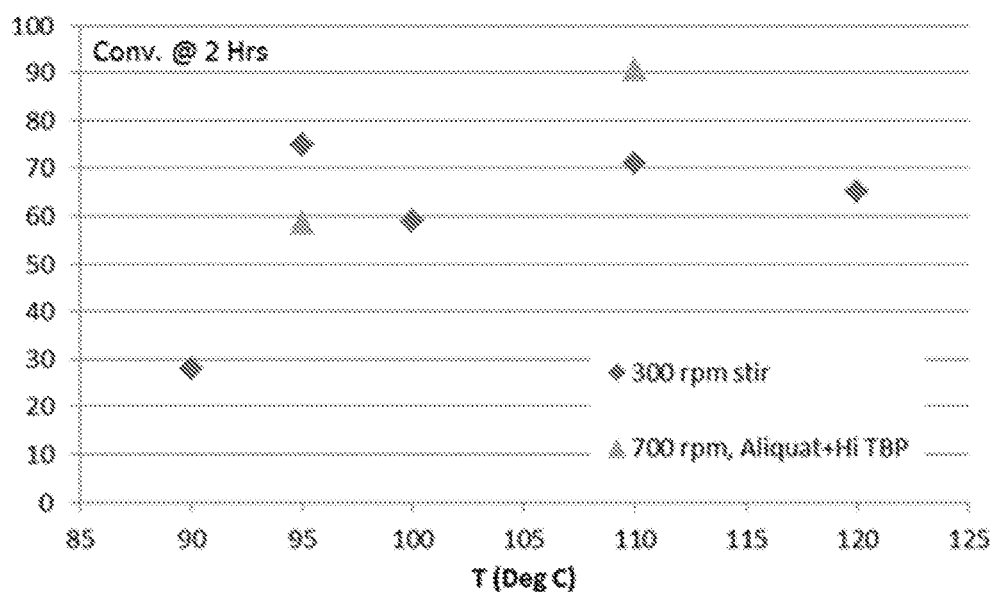
FIG. 10 Presents data for Tet conversion at 2 hours versus temperature in a batch autoclave. The reaction rate was not sensitive to temperature above about 90° C. up to 120° C.

FIG. 3 shows the laboratory autoclave apparatus. FIG. 4 shows typical trends of Tet conversion versus time for baseline runs at two levels of iron metal surface area. FIG. 5 shows selectivity versus conversion for a similar run set. Higher surface area resulted in higher conversion but slightly lower selectivity. FIGS. 6 and 7 show conversion at 2 hours versus amount of free TBP (amount in molar excess compared to iron chloride added) and total TBP, respectively. FIG. 6 clearly shows that kinetics are very slow with no iron metal or no added iron chloride. Although iron chloride is required, it can be generated in situ from iron metal, but kinetics will be slow initially. FIG. 6 shows that, at comparable free TBP levels, high iron chloride addition at the start of a run (high $FeCl_3$:free TBP molar ratio) resulted in slower kinetics. Comparing FIGS. 6 and 7 shows that, given some minimum required levels of iron metal and iron chloride, free TBP (not total TBP) is the primary driver of the reaction kinetics. This is especially apparent by comparing the point for Run 3L in FIG. 7 at 0.836 g total TBP addition (very high) with the corresponding point in FIG. 6. Though total TBP was high, the high level of Fe-TBP complex inhibited kinetics compared to runs at similar free TBP levels in FIG. 6. This indicates that recycle of Fe-TBP complex will not provide the same benefit compared to feeding free TBP. If some method were available to remove iron from a catalyst recycle stream, then catalyst recycle would be more effective, and the amount of fresh TBP feed to the reactor could be reduced. Selectivity to 250fb is plotted versus conversion for selected runs in FIG. 8. Low selectivity at low conversion is typically caused by impurities in the starting reactants, which were included in the selectivity calculation, but became less significant at higher conversion. FIG. 8 shows that at constant free TBP added, reducing the amount of Fe-TBP complex results in lower selectivity. At constant $FeCl_3$ addition, reducing the free TBP added also decreases selectivity. At very high levels of Fe-TBP complex in Run 3L, selectivity started lower but rose to one of the highest selectivity levels observed. With high initial free TBP and zero $FeCl_3$ addition, and after digesting 3 hours to generate Fe-TBP complex (Run 3E), the selectivity started low and then increased. FIG. 9 shows that selectivity is generally higher at higher temperature. Run 2V was the only run that contradicted this conclusion. FIG. 10 shows the reaction rate was generally insensitive to temperature above about 100° C. This deviates from typical Arrhenius behavior, and is likely due to the effect of temperature on ethylene solubility in the liquid phase.

TABLE 1

Test Run Conditions

| Run | Temp (Deg C.) | Press. (psig) | Stir Rate (rpm) | Tet Added (g) | FeCl3 Added (g) | TBP Added (g) | Notes |
|---|---|---|---|---|---|---|---|
| | | | 1.90 cm2 metal (steel exc. 2A) | | | | |
| MRSTU | 110 | 120 | 300 | 17.62 | 0.0762 | 0.2622 | Baseline 1 Average |
| MRSTU | 0 | 0 | 0 | 0.0861 | 0.0017 | 0.0047 | Baseline 1 St. Dev. |
| N | 110 | 120 | 300 | 17.848 | 0.1154 | 0.3273 | High FeCl3 |
| O | 110 | 120 | 300 | 17.301 | 0.0383 | 0.2006 | Low FeCl3 |
| K | 110 | 120 | 300 | 17.613 | 0.0764 | 0.3758 | High TBP, wire after 1 h |
| L | 110 | 120 | 300 | 17.588 | 0.0764 | 0.1341 | Low TBP (v Low free TBP) |
| Y | 110 | 120 | 300 | 17.062 | 0 | 0.1362 | No FeCl3 |
| Z | 110 | 120 | 300 | 17.753 | 0.0592 | 0.2614 | FeCl2 (ferrous) |
| V | 110 | 120 | 300 | 17.578 | 0.0763 | 0.2598 | Pure Fe Chips |

TABLE 1-continued

Test Run Conditions

| Run | Temp (Deg C.) | Press. (psig) | Stir Rate (rpm) | Tet Added (g) | FeCl3 Added (g) | TBP Added (g) | Notes |
|---|---|---|---|---|---|---|---|
| W | 110 | 120 | 300 | 17.635 | 0.0777 | 0.2629 | same chips unwashed |
| 2A | 110 | 120 | 300 | 17.61 | 0.0766 | 0.2612 | 2″ × 1.2 mm pure Fe |
| | | | | | | | 11.49 cm2 metal (pure Fe) |
| 2B-FJP | 110 | 120 | 300 | 17.599 | 0.0766 | 0.2607 | Baseline 2 Avg |
| 2B-FJP | 0 | 0 | 0 | 0.0247 | 0.0011 | 0.0014 | Baseline 2 St. Dev. |
| 2G | 110 | 120 | 300 | 17.317 | 0.0395 | 0.1986 | Low FeCl3 |
| 2H | 110 | 120 | 300 | 17.243 | 0.0194 | 0.1602 | V. Low FeCl3 |
| 2I | 110 | 120 | 300 | 17.2 | 0.02 | 0.0957 | V. Low FeCl3, Low TBP |
| 2K | 110 | 120 | 150 | 17.683 | 0.0775 | 0.2611 | Slow stirring |
| 2L | 110 | 120 | 300 | 17.625 | 0.0578 | 0.2554 | FeCl2, no metal |
| 2M | 100 | 120 | 300 | 17.611 | 0.0779 | 0.2623 | Lower Temp. |
| 2N | 110 | 90 | 300 | 17.579 | 0.0773 | 0.2619 | Lower Press. |
| 2O | 110 | 140 | 300 | 17.573 | 0.0773 | 0.261 | Higher Press. |
| 3E-1 | 110 | 60 | 300 | 17.672 | 0 | 0.2592 | No ethylene |
| 3E-2 | 110 | 130 | 700 | 17.672 | 0 | 0.2592 | FeCl3 made in situ |
| 3K | 110 | 120 | 300 | 17.829 | 0.208 | 0.3649 | Hi TBP, v low free |
| 3L | 110 | 120 | 300 | 17.741 | 0.4231 | 0.8357 | Hi free TBP, v high FeCl3 |
| | | | | | | | 11.49 cm2 metal, Lower FeCl3 and TBP |
| 2R | 110 | 130 | 300 | 17.185 | 0.0237 | 0.116 | Baseline 3 |
| 2S | 120 | 130 | 300 | 17.211 | 0.0236 | 0.1161 | vary Temp |
| 2T | 100 | 130 | 300 | 17.352 | 0.0232 | 0.115 | vary Temp |
| 2U | 90 | 130 | 300 | 17.246 | 0.0234 | 0.1164 | vary Temp |
| 2V | 95 | 130 | 300 | 17.366 | 0.0236 | 0.1161 | vary Temp |
| 2W | 110 | 130 | 700 | 17.191 | 0.023 | 0.1151 | vary Temp, Hi stir |
| 2X | 100 | 130 | 700 | 17.201 | 0.0228 | 0.1139 | vary Temp, Hi stir |
| 2Y | 120 | 130 | 700 | 17.263 | 0.0239 | 0.1168 | vary Temp, Hi stir |
| 2Z | 120 | 130 | 1100 | 17.275 | 0.0237 | 0.1163 | vary Temp, Hi stir |

TABLE 2

Reaction Parameters

| Run | Excess (free) TBP (g) | FeClx/TBP Molar Ratio | Fe Metal Area (cm$^2$) | Fe metal loss (g) | Further Fe metal loss after HCl wash (g) |
|---|---|---|---|---|---|
| | | | 1.90 cm2 metal (steel exc. 2A) | | |
| MRSTU | 0.137 | 0.477 | 1.90 | 0.0045 | |
| MRSTU | 0.003 | 0.007 | 0.00 | 0.0035 | |
| N | 0.138 | 0.579 | 1.90 | 0.0059 | |
| O | 0.138 | 0.313 | 1.90 | 0.0120 | |
| K | 0.250 | 0.334 | 1.90 | 0.0268 | |
| L | 0.009 | 0.935 | 1.90 | 0.0002 | |
| Y | 0.136 | 0.000 | 1.90 | 0.0011 | 0.0036 |
| Z | 0.137 | 0.476 | 1.90 | 0.0083 | |
| V | 0.135 | 0.482 | 2 | 0.0070 | |
| W | 0.135 | 0.485 | 2 | 0.0053 | 0.0079 |
| 2A | 0.135 | 0.481 | 1.92 | 0.0023 | |
| | | | 11.49 cm2 metal (pure Fe) | | |
| 2B-FJP | 0.135 | 0.482 | 11.49 | 0.0102 | 0.0225 |
| 2B-FJP | 0.001 | 0.005 | 0.00 | 0.0018 | 0.0216 |
| 2G | 0.134 | 0.327 | 11.49 | 0.0050 | |
| 2H | 0.128 | 0.199 | 11.49 | | 0.0115 |
| 2I | 0.063 | 0.343 | 11.49 | 0.0022 | 0.0465 |
| 2K | 0.134 | 0.487 | 11.49 | 0.0115 | 0.0173 |
| 2L | 0.134 | 0.475 | 0.00 | | |
| 2M | 0.134 | 0.488 | 11.49 | −0.0040 | 0.0386 |
| 2N | 0.135 | 0.485 | 11.49 | 0.0807 | 0.0276 |
| 2O | 0.134 | 0.486 | 11.49 | 0.0374 | 0.0428 |
| 3E-1 | 0.2592 | 0 | 11.491 | | |
| 3E-2 | 0.259 | 0.000 | 11.49 | 0.0366 | 0.0160 |
| 3K | 0.023 | 0.936 | 11.49 | −0.0043 | 0.0056 |
| 3L | 0.141 | 0.831 | 11.49 | −0.0183 | 0.0423 |
| | | | 11.49 cm2 metal, Lower FeCl3 and TBP | | |
| 2R | 0.077 | 0.335 | 11.49 | 0.0097 | 0.0092 |
| 2S | 0.077 | 0.334 | 11.49 | 0.0133 | 0.0102 |
| 2T | 0.077 | 0.331 | 11.49 | 0.0063 | 0.0190 |
| 2U | 0.078 | 0.330 | 11.49 | 0.0043 | 0.0102 |
| 2V | 0.077 | 0.334 | 11.49 | −0.0160 | 0.0481 |
| 2W | 0.077 | 0.328 | 11.49 | 0.0098 | 0.0151 |
| 2X | 0.076 | 0.329 | 11.49 | −0.0050 | 0.0245 |
| 2Y | 0.078 | 0.336 | 11.49 | 0.0099 | 0.0095 |
| 2Z | 0.077 | 0.335 | 11.49 | 0.0056 | 0.0173 |

TABLE 3

Results

| Run | Conv @2 Hrs (%) | Selectivity @2 Hrs | Final Conv. (%) | Final Select. (%) | Final Time (Hr) |
|---|---|---|---|---|---|
| | | 1.90 cm2 metal (steel exc. 2A) | | | |
| MRSTU | 43.56 | 98.44 | 57.52 | 98.31 | 2.83 |
| MRSTU | 13.36 | 0.03 | 17.25 | 0.10 | 0.46 |
| N | 48 | 98.78 | 68.35 | 98.65 | 3.00 |
| O | 69 | 97.76 | 87.87 | 97.44 | 2.83 |
| K | | | 94.04 | 97.73 | 1.75 |
| L | 19 | | 24.57 | | 2.75 |
| Y | 12 | | 19.06 | | 3.00 |
| Z | 54 | | 79.43 | | 3.00 |
| V | 63.3 | | 84.93 | | 3.07 |
| W | 40.3 | | 59.69 | | 3.02 |
| 2A | 32.8 | | 47.67 | | 3.00 |

TABLE 3-continued

Results

| Run | Conv @2 Hrs (%) | Selectivity @2 Hrs | Final Conv. (%) | Final Select. (%) | Final Time (Hr) |
|---|---|---|---|---|---|
| 11.49 cm2 metal (pure Fe) | | | | | |
| 2B-FJP | 80.58 | 97.96 | 90.88 | 97.69 | 2.62 |
| 2B-FJP | 8.80 | 0.18 | 6.87 | 0.32 | 0.42 |
| 2G | 87 | 97.36 | 90.3 | 97.36 | 2.21 |
| 2H | 86.5 | 96.86 | 96.57 | 95.43 | 3.00 |
| 2I | 50 | 96.35 | 74.62 | 96.19 | 3.05 |
| 2K | 86 | | 95.2 | | 3.00 |
| 2L | 15.6 | | 15.6 | | 2.10 |
| 2M | 87.25 | | 97.12 | | 2.87 |
| 2N | 95.63 | 97.11 | 99.89 | 95.04 | 2.68 |
| 2O | 98.5 | | 99.9 | | 2.68 |
| 3E-1 | | | | | 3.00 |
| 3E-2 | 52 | 96.10 | 67.26 | 96.57 | 2.90 |
| 3K | 10.87 | 97.79 | 18.03 | 98.66 | 3.57 |
| 3L | 64.65 | 97.40 | 92.47 | 97.84 | 3.60 |
| 11.49 cm2 metal, Lower FeCl3 and TBP | | | | | |
| 2R | 71 | 97.20 | 89.39 | 96.91 | 4.28 |
| 2S | 65 | 97.13 | 87.48 | 96.77 | 4.00 |
| 2T | 59 | 96.60 | 98.07 | 95.44 | 4.80 |
| 2U | 28 | 96.24 | 71.79 | 96.14 | 5.18 |
| 2V | 75 | 97.00 | 98.51 | 95.6 | 5.00 |
| 2W | 76 | 97.15 | 95.43 | 96.57 | 4.75 |
| 2X | 48 | 96.57 | 95.23 | 95.7 | 5.00 |
| 2Y | 76 | 97.09 | 94.23 | 96.41 | 5.00 |
| 2Z | 63 | | 93.23 | | 4.50 |

Example 3: Use of a Combination of Fe+2/+3 without Metallic Fe

To test whether 1,1,1,3-tetrachloropropane (250fb) can be prepared from Tet+ethylene without the use of metallic iron, the baseline case (runs 2B-2F, 2J, and 2P) from Example 2 was performed essentially as detailed above except that Fe(0) wire was not used. Rather, $FeCl_2$ will be used at the same molar amount as $FeCl_3$ in the baseline runs. Run 2L had no iron metal, but contained ferrous iron instead of ferric. At 2 hrs. residence time, a Tet conversion of 16% is achieved with 98.1% selectivity (see Table 1). Fe(0) is required for reactor productivity and $FeCl_2$ alone provides about 4× slower kinetics compared to $FeCl_3$ in combination with Fe(0) in baseline runs.

Example 4: Generation of Active Species from Metallic Iron and TBP in a Separate Step and Feed to Main Reactor Experimental conditions were similar to those used in the baseline cases (2B-2F, 2J, and 2P) detailed in Example 2 except that $FeCl_x$ was not used. Rather, a solution of Tet and TBP was heated in the presence of Fe(0) at 100° C. for about 3 hours prior to adding ethylene and starting the reaction. The Tet conversion was 52% after 2 hours and 67% after 2.9 hours. Selectivity was greater than 96%. Reaction rate was significantly slower than the baseline cases, but adequate for commercial use.

Figure 15:
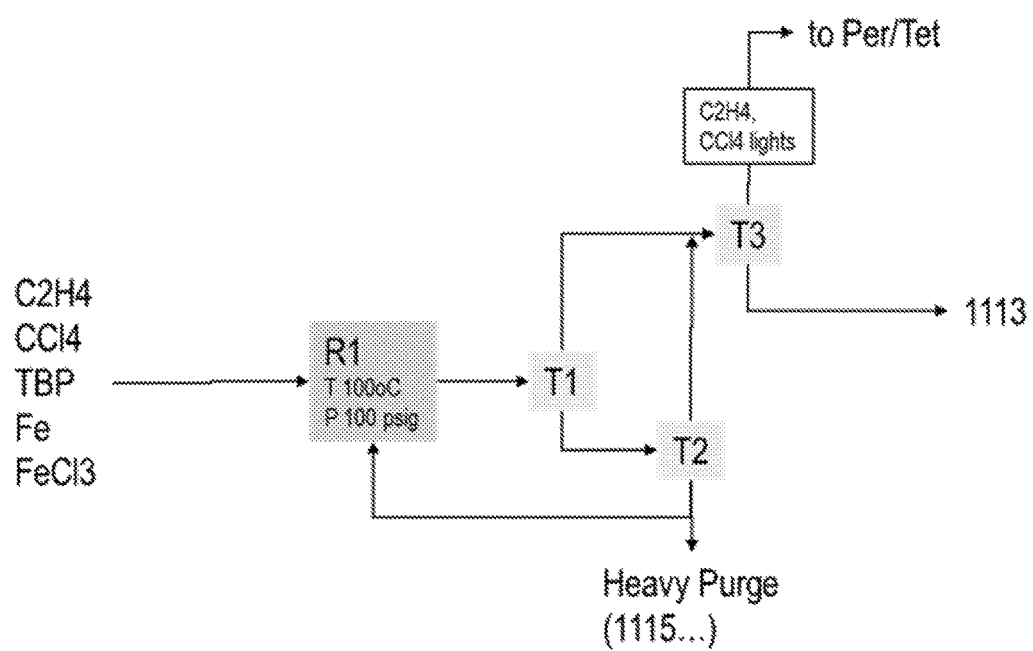
FIG. 15 presents a simplified diagram of a continuous process for producing 1,1,1,3-tetrachloropropane comprising columns T1, T2, and T3.
Figure 16:
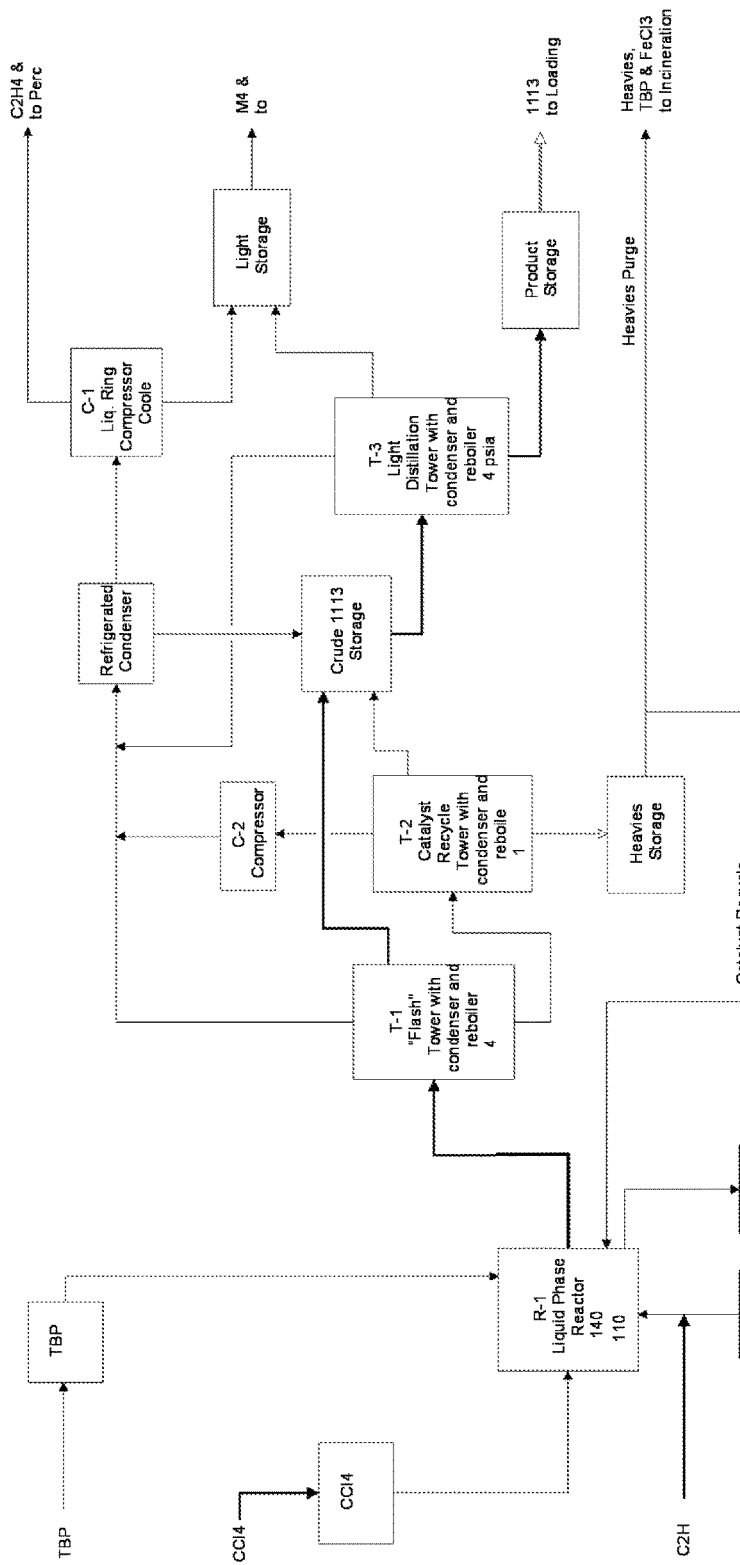
FIG. 16 presents a block diagram of a continuous process for producing 1,1,1,3-tetrachloropropane (1113) with 3 distillation columns.
Figure 17:
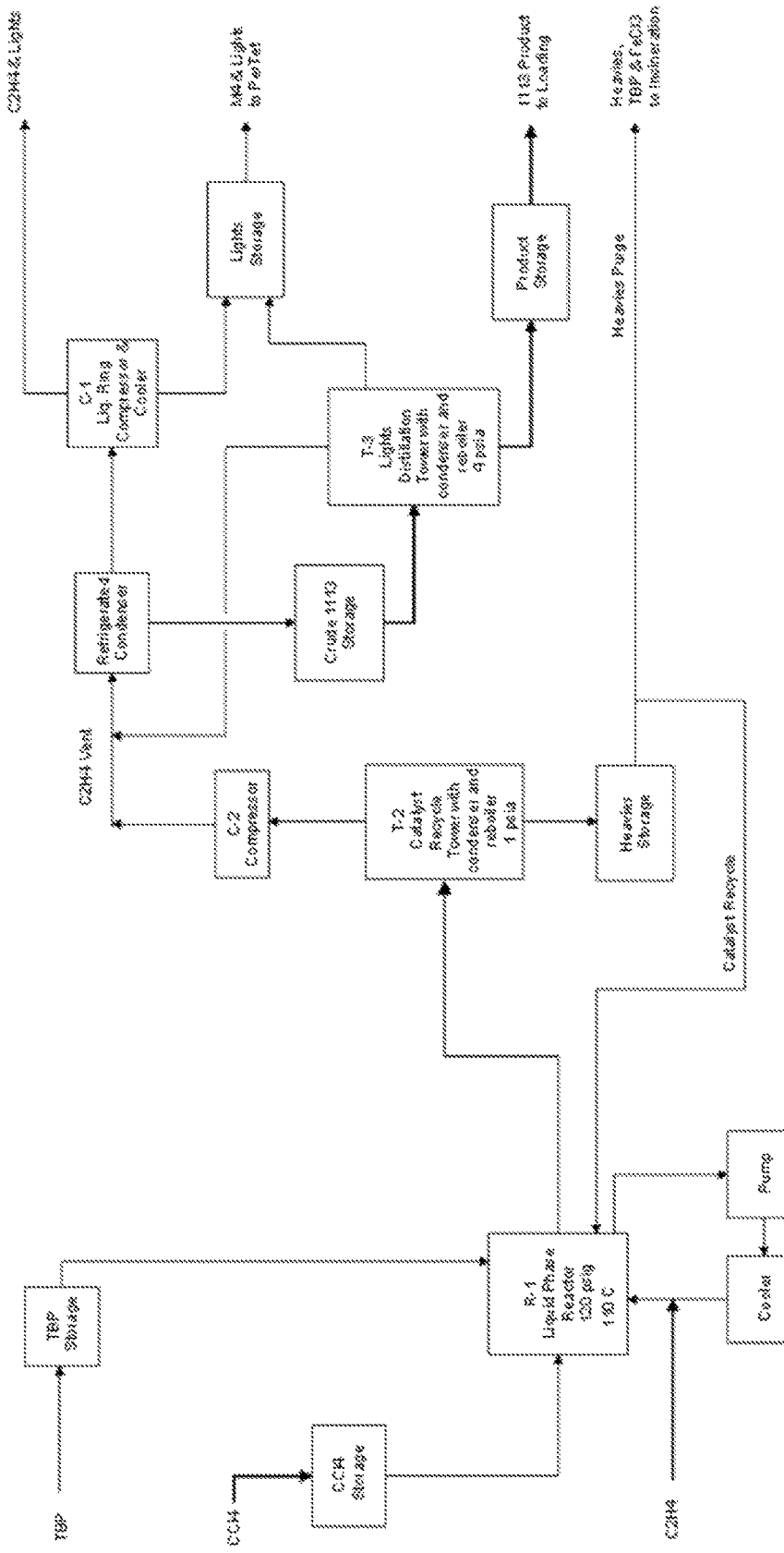
FIG. 17 presents a block diagram of a continuous process for producing 1,1,1,3-tetrachloropropane (1113) with a side draw distillation column to reduce the number of columns from 3 to 2.
Figure 18:
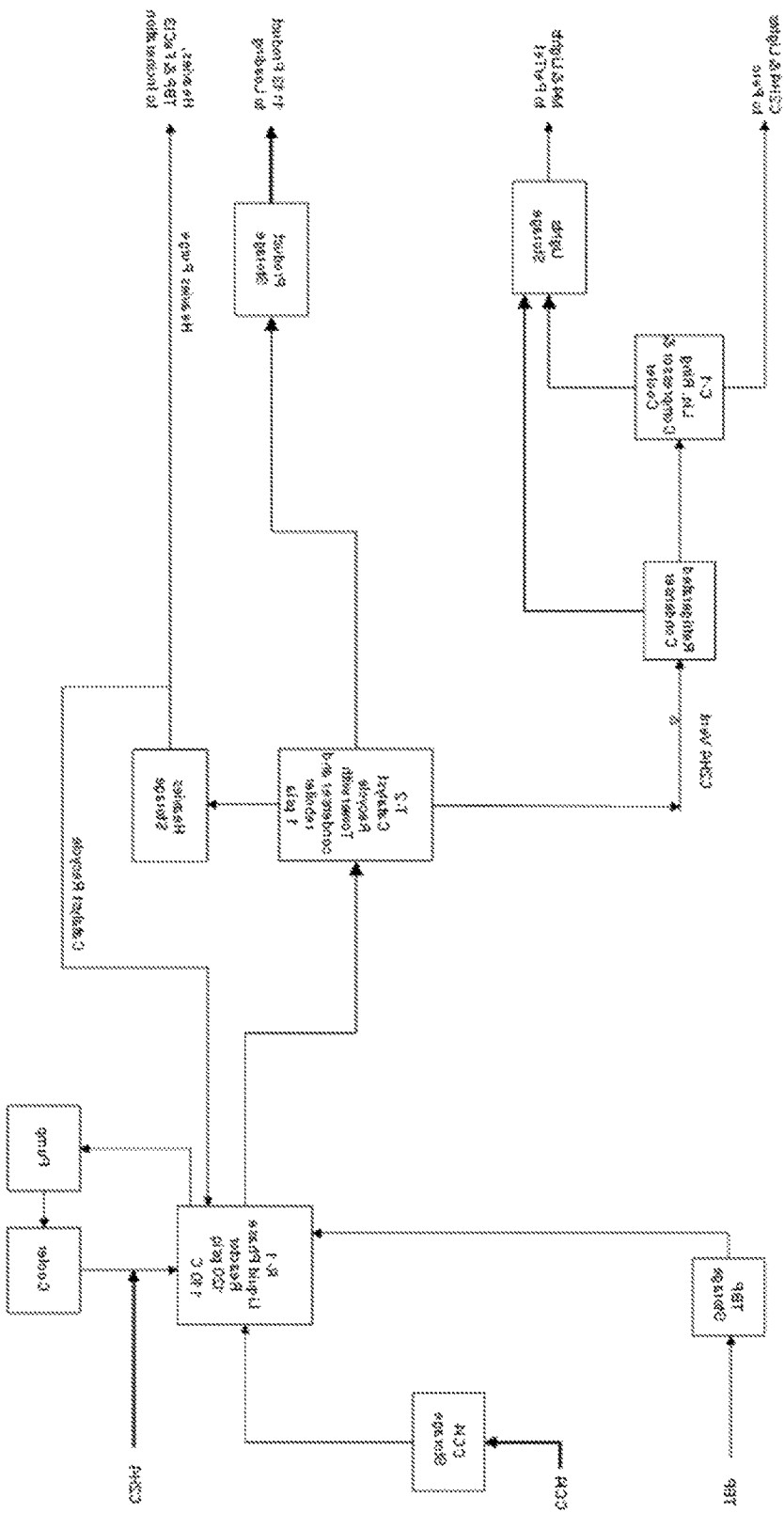
FIG. 18 presents a block diagram of a continuous process for producing 1,1,1,3-tetrachloropropane (1113) with a side draw distillation column to reduce the number of columns from 3 to 1.

Example 5: Continuous Process for the Production of 1,1,1,3-Tetrachloropropane or 1,1,1,3,3-Pentachloropropane The following example details the production of 1,1,1,3-tetrachloropropane (1113 or 250fb) or 1,1,1,3,3-pentachloropropane (11133 or 240fa) by reacting $CCl_4$ with ethylene to produce 1113 or $CCl_4$ with vinyl chloride (VCM) to produce 11133 using a catalyst system consisting of $FeCl_3$ and/or $FeCl_2$, alkyl phosphate, and non-powder Fe (e.g., metal insert) in a continuous flow reactor with internal recirculation as a means of mixing the reactants. FIG. 15 presents a simplified diagram of the process for producing 1113. FIG. 16 presents a more detailed block diagram of the process for producing 1113. FIG. 17 and FIG. 18 show alternate processes using fewer distillation columns with lower capital cost.

Figure 11:
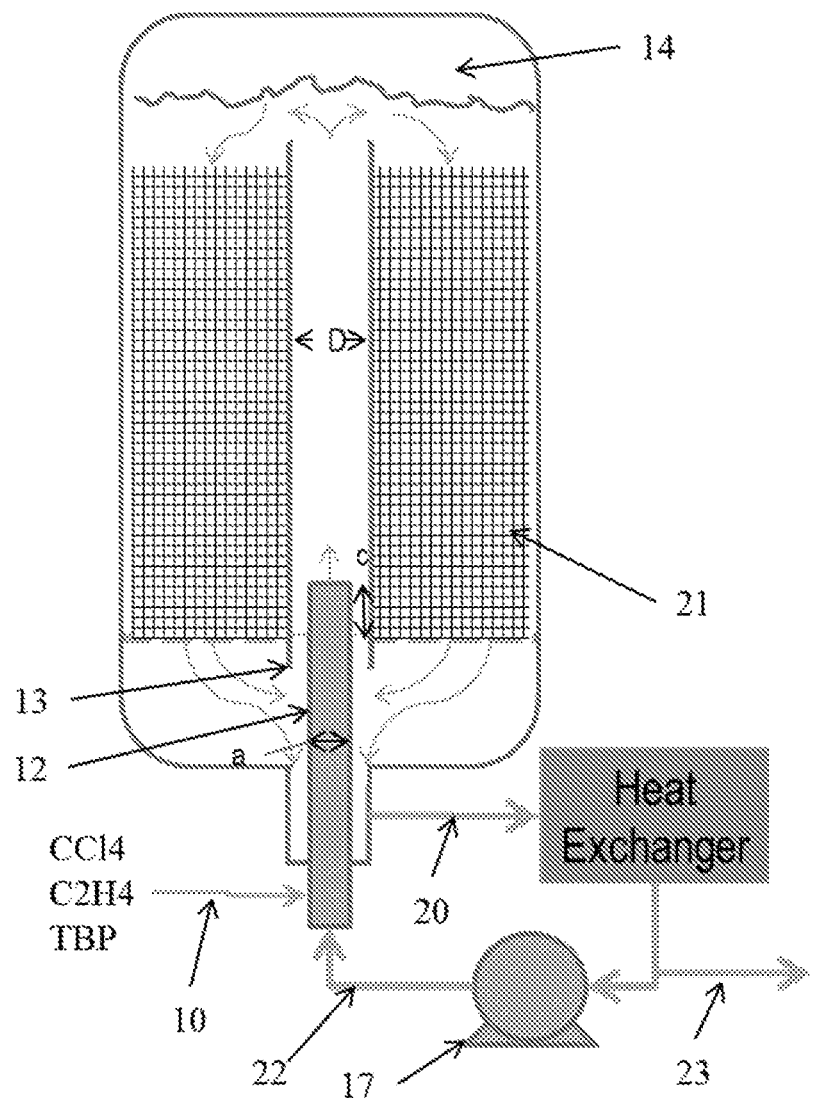
FIG. 11 illustrates a potential reactor design with reaction liquid circulated through a liquid jet that injects the liquid into the bottom of the reactor to induce internal reactor circulation.

A proposed reactor design for the production of 250fb (1,1,1,3-tetrachloropropane or 1113) is shown in FIG. 11. Here the reactants $C_2H_4$, $CCl_4$, and catalyst promoters TEP (Triethylphosphate) or TBP (tributylphosphate) are fed in line 10 into a sparger tube 12. The feed sparger tube 12 is connected to center tube 13 inside the reactor chamber 15 with dimension as shown in Table 4. The reactants flow upward tube center 13 and leaves the tube into the top of the reactor chamber where the light reactant such as ethylene is collected on top of the gas-phase zone 14. The reactant jets exiting tube 13 at velocity above turbulent (Re#>3000) such that mixing between the light reactant ethylene and the liquid reactant ($CCl_4$) is facilitated. As appreciated by one of skill in the art, the flow may be turbulent or non-turbulent, provided mixing occurs. The mixed reactants then flow down into a catalyst Fe(0) zone 21 supported as a fixed bed. The porosity of the bed is very high as shown in Table 5 since the Fe(0) can be in the form of wires, structured or unstructured packing. Table 5 also shows the potential dimension of the Fe(0) bed 21 as a function of center tube 13 ID. The reactants are converted into the products after or during flowing through the bed 21 and exiting the reactor at the annulus region at the bottom of the reactor through the exit line 20 which is driven by the pump 17. A portion of the product exiting the pump is taken for purification through line 23 and the rest is recycled back to the reactor via line 22 after cooled or heated by exchanger 18 to maintain the desired temperature as shown in Table 4. Table 4 also shows other desired operating condition to produce 30KTA of product shown in Table 6. The mass flow of the recycled stream 22 is desirably greater than 3× of the fresh reactant flow in line 10.

TABLE 4

Properties of the Reactor Chamber

| | |
|---|---|
| ID (ft) | 8 |
| Height (ft) | 24 |
| liquid level % | 90% |
| Productivity (gr/L/hr.) | 150.5 |
| 250FB production rate (KTA) | 30 |
| $CCl_4$ conversion | 67% |
| $CCl_4/C_2H_4$ molar | 1.5 |
| Fresh $CCl_4$ flow rate (#/hr.) | 6845 |
| Fresh $C_2H_4$ flow rate (#/hr.) | 832 |
| Pressure (psig) | 100 |
| Temperature (° C.) | 100 |

TABLE 5

Properties of the Fe(0) Bed

| | |
|---|---|
| Fe(0) tons/y | 5 |
| #Fe(0) | 11020 |
| Fe(0) bed porosity | 0.9 |
| Fe(0) bed volume (ft³) | 224 |

TABLE 5-continued

| Properties of the Fe(0) Bed | | | | |
|---|---|---|---|---|
| Inner tube ID (ft) | 0.5 | 1 | 1.5 | 2 |
| Fe(0) Bed length (ft) | 4.5 | 4.5 | 4.6 | 4.8 |

TABLE 6

| Operating Conditions | | |
|---|---|---|
| Product flow rate | | wt % |
| $CCl_4$ (#/hr.) | 3423 | 29.0% |
| $C_2H_4$ (#/hr.) | 0 | 0.0% |
| 1113 (#/hr.) | 7688 | 65.1% |
| 1115 (#/hr.) | 467 | 4.0% |
| $FeCl_3$ (#/hr.) | 92 | 0.8% |
| TBP (#/hr.) | 148 | 1.3% |
| total product flow rate (#/hr.) | 11818 | |

Figure 12:
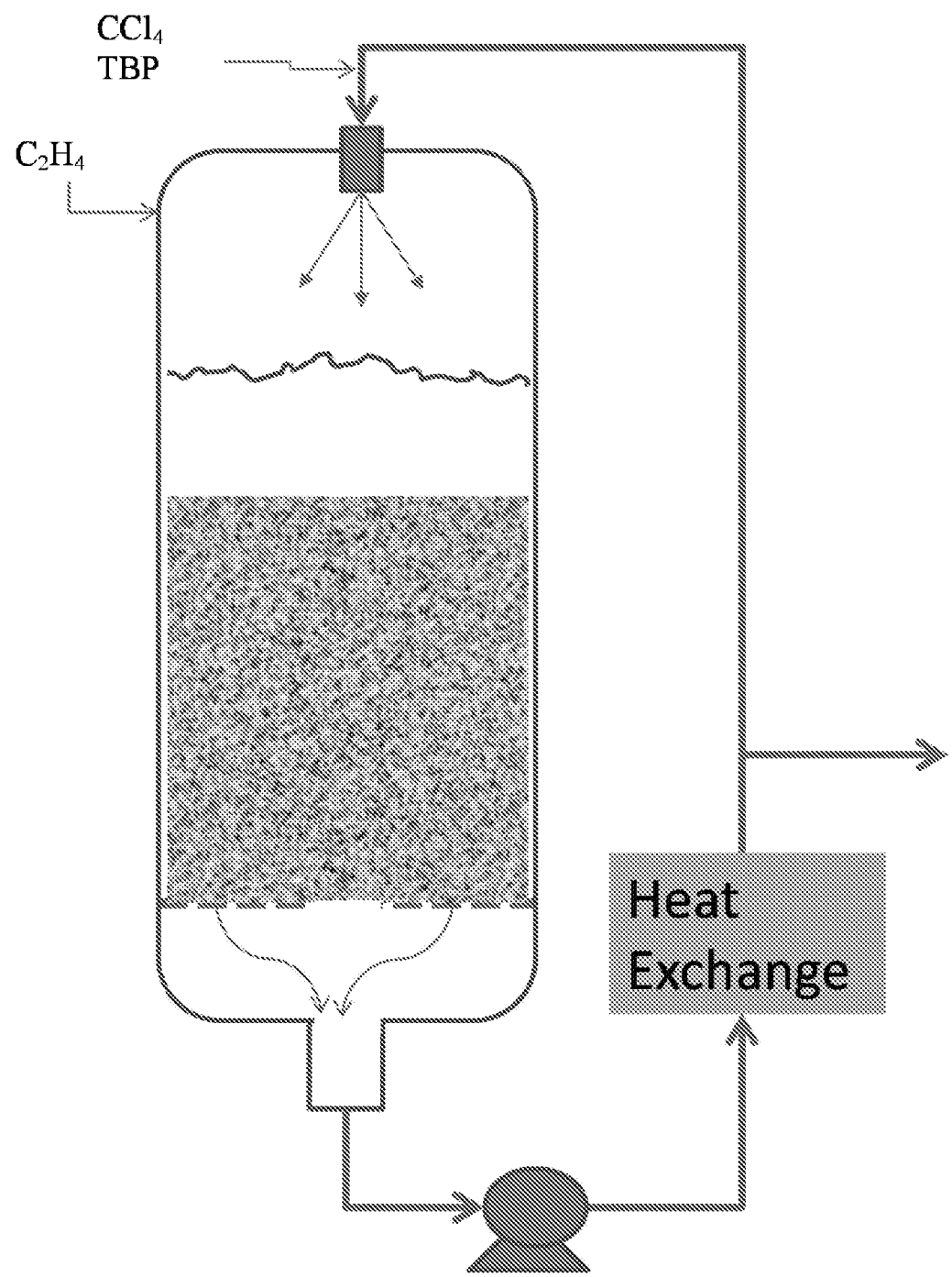
FIG. 12 illustrates an alternate reactor design with reaction liquid circulated through a liquid jet that injects the liquid into the top of the reactor through the gas phase and into the liquid phase.

FIG. 12 presents a diagram of an alternate reactor design that has properties similar to those detailed in Tables 4-6, except that there is no inner tube through the catalyst bed and the liquid circulation stream is returned to the top of the reactor through a nozzle that directs liquid through the gas phase and into the liquid phase of the reactor. The nozzle can be a spray nozzle to provide gas/liquid mass transfer, or a jet nozzle that forces gas into and creates turbulence in the liquid phase.

Figure 13:
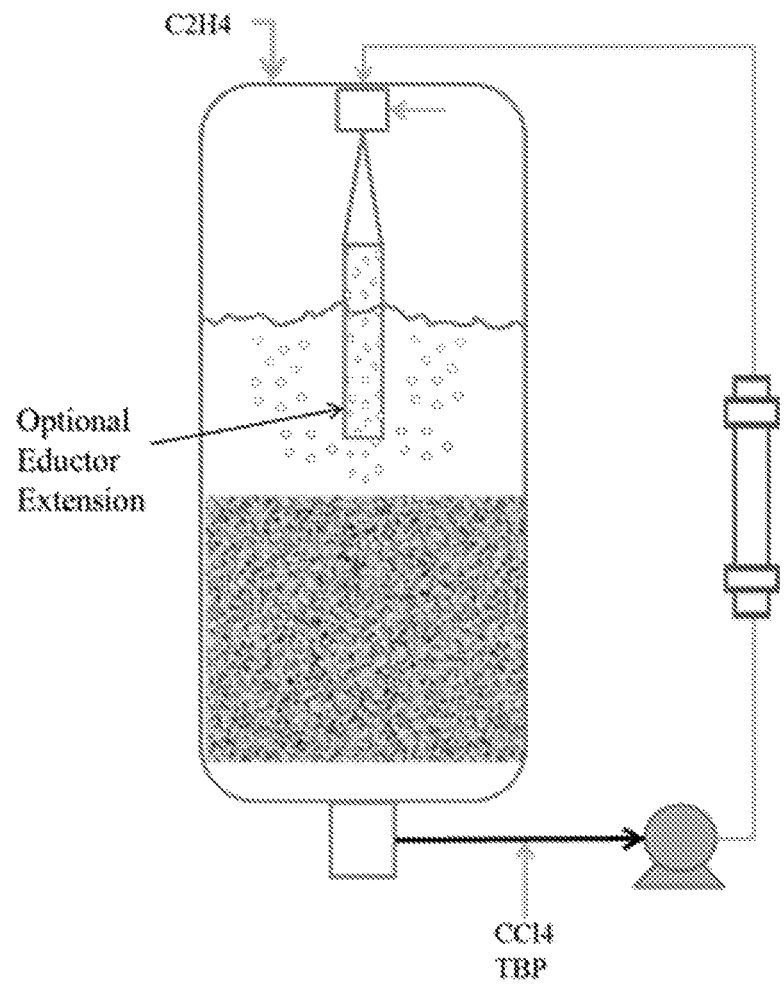
FIG. 13 presents an alternate reactor design with an educting nozzle that mixes gas from the top of the reactor with a liquid circulation stream and injects the resulting mixture into the top of the liquid phase of the reactor. The extension into the liquid phase is optional into a draft tub at the bottom of the reactor to induce liquid circulation in the reactor.

Another reactor design is also shown in FIG. 13. This reactor uses a jet educator and an external heat exchanger to control the reaction temperature Tet, TBP, and optionally $FeCl_3$ are fed into the pump suction, or can be added directly to the reactor. The circulation stream from the pump is fed as a motive fluid into the eductor, which is mounted inside the head of the reactor in the gas phase. Gas from the head of the reactor is pulled into the eductor and mixes with the liquid feed to the eductor. The resulting mixture exits the eductor and is directed into the liquid phase inside the reactor. An optional extension tube on the exit of the eductor can be used to force the gas phase in the mixture leaving the eductor into the liquid phase in the reactor, thereby creating bubbles.

TABLE 7

| Alternate Fe(0) Bed Properties | | |
|---|---|---|
| F3 density (#/in³) | 0.284 | |
| #Fe/#1113 | 0.174% | |
| 250fb production (KTA) | 30 | 30 |
| No. reactors | 2 | 1 |
| #Fe(0)/reactor | 57407 | 114815 |
| Fe(0) bed porosity | 0.5 | 0.5 |
| Fe(0) bed volume (ft³) | 117.0 | 234.0 |
| Fe(0) bed ID (ft) | 4 | 5 |
| FE(0) bed length *ft) | 9.3 | 11.9 |

Figure 14:
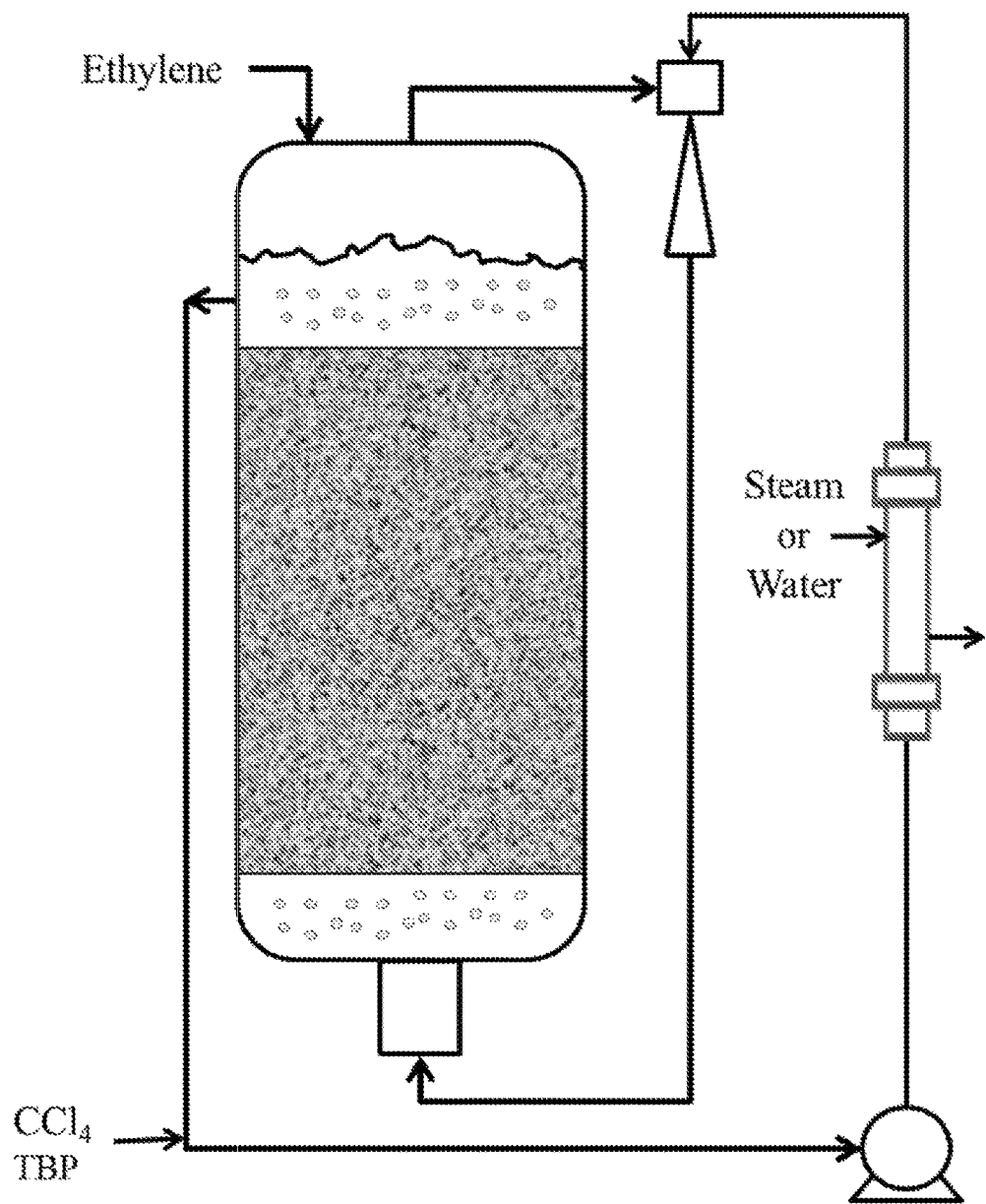
FIG. 14 presents an alternate reactor design with an educting nozzle that mixes gas from the top of the reactor with a liquid circulation stream and injects the resulting mixture into the bottom of the reactor, wherein liquid and gas bubbles travel upward through the bed.

Still another reactor design is shown in FIG. 14. This design is similar to that shown in FIG. 13, except the eductor is mounted outside the reactor and the liquid circulation stream is withdrawn from the liquid phase in the top of the reactor and the eductor exit, containing a gas/liquid mixture, is directed to the bottom of the reactor below the iron catalyst bed. Ethylene can be fed to the top of the reactor and Tet, TBP and, optionally, $FeCl_3$ can be fed into the pump suction.

FIG. 16 shows a process design that can be used with any of the reactor designs presented above. T1 is a flash tower with a condenser and a reboiler for separation of 1113 and 1115. The reboiler temperature may be run at 90° C. The liquid residence time may be less than 1 day. The pressure may be 200 Torr or 4 psia.

T2 is a catalyst recycle tower with a condenser and a reboiler for heavy purge (i.e., 1115) and catalyst recycle. The reboiler temperature may be run at 110° C. The liquid residence time may be less than 6 hours at a pressure may be 50 Torr or 1 psia. There may be a 10% purge rate of the heavies stream to incineration.

T3 is a lights distillation tower with a condenser and a reboiler for separation of Tet and 1113. The reboiler temperature may be run at 110° C. The liquid residence time may be less than 4 hours at a pressure of 200 Torr or 4 psia.

Example 6: Modification of Continuous Process

The continuous process detailed in Example 5 and depicted in FIGS. 15 and 16 was modified by injecting Tet (a low-boiling liquid) into distillation reboiler of T-2 to facilitate boil-up at lower bottom temperature (to minimize reboiler fouling) and/or higher pressure (to reduce vacuum pump size and energy). In addition, higher pressure reduced the size of the distillation column and hence potentially reduces the capital cost.

Table 8 presents results from a standard run and Tet injection runs under two different conditions.

TABLE 8

| Process Conditions. | | | |
|---|---|---|---|
| | Standard | Tet Inj - low pressure | Tet Inj - high pressure |
| Tet Injection to Reboiler (kg/hr.) | 0 | 1000 | 1000 |
| Pressure Overhead (mm Hg) | 50 | 50 | 100 |
| Temperature Overhead (° C.) | 77.6 | 16.9 | 32.4 |
| Temperature Bottom (° C.) | 93.7 | 75.4 | 94.2 |
| Reflux Ratio (Molar) | 1 | 0.35 | 0.45 |
| Column Diameter (m) | 0.827 | 0.931 | 0.793 |
| Flow Bottoms (kg/hr.) | 194.2 | 197.7 | 197.7 |
| 1113TCP Bottoms (% Mass) | 0.392 | 0.375 | 0.371 |
| 1115TCPN Overhead (ppm mass) | 3 | 0.5 | 1 |
| 1335TCPN Overhead (ppm mass) | 673 | 668 | 607 |

Example 7: Modification of Continuous Process

The continuous process detailed in Example 5 and depicted in FIGS. 15 and 16 was modified by injecting Tet (a low-boiling liquid) into distillation reboiler of T-1 to facilitate boil-up at lower bottom temperature (to minimize reboiler fouling). Column feed remained constant. Table 9 presents results from a standard run and Tet injection run.

TABLE 9

| Process Conditions without and with Tet injection | | | | | |
|---|---|---|---|---|---|
| | Column Feed | Tet 0 to T-1 with Reflux Ratio 5 | | Tet 1500 kg/Hr to T-1 with Reflux Ratio 0.95 | |
| | R1LIQ | D1OVH | D1BTM | D1OVH | D1BTM |
| Temperature C. | 110 | 45 | 118.2 | 45 | 100.8 |
| Pressure bar | 11.36 | 0.27 | 0.27 | 0.27 | 0.27 |
| Mass Flow kg/hr | 456.61 | 386.62 | 70.00 | 1886.61 | 70.00 |

TABLE 9-continued

Process Conditions without and with Tet injection

| | Column Feed | Tet 0 to T-1 with Reflux Ratio 5 | | Tet 1500 kg/Hr to T-1 with Reflux Ratio 0.95 | |
|---|---|---|---|---|---|
| | R1LIQ | D1OVH | D1BTM | D1OVH | D1BTM |
| Mass % | | | | | |
| M4 | 0.155 | 18.11 | trace | 83.05 | 0.055 |
| 1113TCP | 0.794 | 79.05 | 0.82 | 16.39 | 0.764 |
| 1115TCPN | 0.02 | trace | 0.131 | trace | 0.132 |
| 1335TCPN | 0.007 | trace | 0.044 | trace | 0.044 |

Example 8: Purification Using $C_2H_4$ to Improve Purification of 250FB

The use of $C_2H_4$ to improve purification of 250FB finishing column T-3 is compared with conventional vacuum distillation performance as depicted in FIG. 16. This method shows that similar product quality can be obtained with 23° C. lower reboiler temperature. This method also suggests potentially significant lower reboiler fouling and lower energy required for the reboiler operation.

Table 10 presents results from a standard run with $C_2H_4$ injection.

| | Vacuum Distillation | Stripping |
|---|---|---|
| T3 BOTTOM | PRODUCT | PRODUCT |
| Temperature ° C. | 114.6 | 91.4 |
| Pressure bar | 0.27 | 0.27 |
| Vapor Frac | 0 | 0 |
| Mass Flow kg/hr | 436 | 478 |
| Mole Frac | | |
| ETHYLENE | trace | 2 PPM |
| M3 | trace | 42 PPB |
| M4 | trace | 0.103 |
| PER | 422 PPM | 704 PPM |
| 1113TCP | 0.992 | 0.889 |
| 1115TCPN | 511 PPB | 458 PPB |
| CLBA | trace | 238 PPM |
| EDC | trace | 808 PPM |
| 111TCPA | 735 PPM | 657 PPM |
| HCE | 868 PPM | 777 PPM |
| 11133C3 | 99 PPM | 88 PPM |
| 11223C3 | 82 PPM | 74 PPM |
| 1117C7 | trace | trace |

Example 9: Process for Producing 250 FB Comparing Two and Three Distillation Columns FIG. 17 presents a process of producing 250FB from the reaction of $CCl_4$ and $C_2H_4$ where two distillation columns are used to purify the product. The number of theoretical stages for distillation columns T-2 and T-3 is 17 and it has been kept the same as the case with 3 distillation columns where an additional Column T-1 also uses 17 stages. The crude liquid product from reactor R-1 is fed to the first distillation T-2 where the bottom product comprising heavy byproduct is taken from the T-2 bottom stream at 81° C. About 75% of T-2 bottom stream is recycled to R-1 whereas the rest is purged from the process. The overhead stream of T-2 at −13° C. is compressed and combined with T3 overhead vapor stream (T3OH-V) into a refrigerated condenser at 0.1° C. The condensed liquid is fed to the T-3 column where the product with 99.2% purity by mole is obtained in the T-3 bottom stream. The T-3 overhead liquid stream consisting mostly $CCl_4$ is sent to lights liquid storage and sent further to a down-stream process to make Perc. The vent stream comprising ethylene from the overhead of C-1 liquid Ring compressor may also be sent to Perc. Note that the T-2 bottom heavy stream also includes the TBP-FeClx (where x is 1, 2, or 3) complexes and their compositions are not shown here. Table 11 presents two columns that provide 250FB with the same purity as that of three columns and thus this provides a process with lower operating and capital costs.

TABLE 11

Comparison between Two and Three Distillation Columns

| | 3column | 2Columns |
|---|---|---|
| Temperature ° C. | 114.6 | 114.3 |
| Pressure bar | 0.27 | 0.27 |
| Mass Flow kg/hr | 436 | 434 |
| Mass Frac | | |
| M4 | trace | 504 PPM |
| PER | 384 PPM | 729 PPM |
| 1113TCP | 0.989 | 0.989 |
| 1115TCPN | 588 PPB | trace |
| CLBA | trace | 2 PPM |
| EDC | trace | 47 PPM |
| 111TCPA | 594 PPM | 597 PPM |
| HCE | 0.001 | 678 PPM |
| 11133C3 | 117 PPM | 39 PPM |
| 11223C3 | 97 PPM | 8 PPM |

Example 10: Process for Preparing 250 FB Using One Distillation Column

FIG. 18 presents the process for producing 250FB using only one distillation column. The stream vectors for each stream are provided with the mole fraction of component larger than 10 ppm. Table 12 compares the purity level of the product using 3 columns vs. 1 column where the product is taken from a side stream from liquid of stage 23 from the top of the distillation column with 30 stages. This shows that about only less than 1% lower purity is achieved with only one column compared to using 3 columns.

Table 12 presents results from a standard run comparing 3 Columns versus a 1 Column for Purification of the 250FB.

| | 3 Columns | 3 in 1 Column |
|---|---|---|
| Temperature C. | 114.6 | 78.2 |
| Pressure bar | 0.27 | 0.07 |
| Mass Flow kg/hr | 436 | 425 |
| Mass Frac | | |
| M3 | trace | trace |
| M4 | trace | 1 PPM |
| PER | 384 PPM | 357 PPM |
| 1113TCP | 0.989 | 0.980 |
| 1115TCPN | 588 PPB | 0.01 |
| CLBA | trace | 3 PPB |
| EDC | trace | 60 PPB |
| 111TCPA | 594 PPM | 436 PPM |
| HCE | 0.001 | 0.002 |
| 11133C3 | 117 PPM | 313 PPM |
| 11223C3 | 97 PPM | 567 PPM |
| 1117C7 | trace | 204 PPM |

Example 11: Fe Removal by Ion Exchange

To a 100 cc beaker was added 6.84 g crude 250fb from one of the autoclave runs. The sample had 1050 ppm by weight total Fe as Fe-TBP complex. To this was added 0.33 g Dowex 50 WX2 (H⁺ form) which contained about 40% water (original resin weighed 0.93 g and contained about 79% water and was partially dried with nitrogen). The contents of the beaker was stirred for 30 m and analyzed for total Fe concentration, which was 253 ppm. It is presumed but not proved that the increased level of free TBP, if recycled to the 250fb reactor, will be more active than recycling the TBP that was predominantly in the form of Fe-TBP complex.

What is claimed is:

1. A process for producing halogenated alkanes, the process comprising:
   a. forming a reaction mixture in a reactor by contacting: a liquid phase comprising a halogenated methane comprising at least one chlorine atom, at least one phosphorus containing compound comprising a trialkylphosphate, a trialkylphosphite, or combinations thereof; and at least one catalyst comprising a metal, metal salt, or combinations thereof; an alkene, halogenated alkene, or combinations thereof, thereby forming a reaction mixture; wherein the alkene, halogenated alkene, or combinations thereof and is at least partially absorbed into the liquid phase;
   b. stirring the reaction mixture;
   c. heating the reaction mixture; and
   d. producing halogenated alkanes and heavy by-products;
   wherein there is a gas phase above the reaction mixture and wherein the order of steps b. and c. may be switched or conducted at the same time;
   wherein the process further comprises at least one of the following:
   (I) stirring the reaction mixture comprising jet mixing;
   (II) the process further comprises step e., wherein step e. comprises:
      i. transferring at least part of the reactor contents into a first separator where two product streams (a) and (b) are formed: wherein product stream (a) comprises the halogenated alkane, halogenated methane comprising at least one chlorine atom, and an alkene or halogenated alkene; wherein product stream (b) comprises the heavy by-products, the at least one phosphorous containing compound, and at least one catalyst;
      ii. contacting at least a portion of product stream (b) with an ion exchange resin to form product stream (c) wherein product stream (c) contains less of at least one metal ion when compared to product stream (b); and
      iii. returning at least a portion of product stream (c) to the reactor; and
   (III) the process further comprises step f, wherein step f comprises:
      i. transferring at least part of the reactor contents into a first separator where two product streams (a) and (b) are formed, wherein product stream (a) comprises the halogenated alkane, halogenated methane with at least one chlorine atom, and the alkene, halogenated alkene, or combinations thereof and product stream (b) comprises the heavy by-products, the at least one phosphorous containing compound, and the at least one catalyst;
      ii. transferring at least a portion of product stream (b) back into the reactor;
      iii. transferring product stream (a) into a second separator and producing two product streams (d) and (e), wherein product stream (d) comprises the halogenated alkane and product stream (e) comprises halogenated methane with at least one chlorine atom and the alkene, halogenated alkene, or combinations thereof;
      iv. optionally introducing at least a portion of product stream (e) into the reactor;
      wherein at least one of the first separator and the second separator comprises a reboiler, bottom stage, or both;
      wherein the first separator or the second separator may be separate or contained in a single separation device;
      wherein when the first and second separation devices are contained in a single separation device, the single separation device will separate at least a portion of product stream (d) from product streams (b) and (e);
      wherein one or more of the separators is a multistage distillation column in which a stripping gas or low boiling stripping liquid comprising an alkane, alkene, halogenated alkane, halogenated alkene, or nitrogen is introduced into the first separator reboiler, the second separator reboiler, the first separator bottom stage, the second separator bottom stage, or combinations thereof; and wherein the stripping gas or low boiling stripping liquid is in addition to any components originating from the reactor.

2. The process of claim 1, wherein the process comprises (I).

3. The process of claim 1, wherein the process comprises (II).

4. The process of claim 1, wherein the process comprises (III).

5. The process of claim 1, wherein jet mixing withdraws a portion of the liquid phase of the reaction mixture from the reactor and pumps the liquid phase back into the reactor through at least one nozzle to create a jet, thereby creating turbulence in the liquid phase.

6. The process of claim 1, wherein jet mixing withdraws a portion of the liquid phase of the reaction mixture from the reactor and pumps the liquid phase back into the reactor through at least one nozzle to create a jet directed through the gas phase and into the liquid phase of the reaction mixture, thereby entraining gas into the liquid phase.

7. The process of claim 1, wherein jet mixing withdraws a portion of the liquid phase of the reaction mixture from the reactor and pumps the liquid phase back into the reactor through at least one gas educting nozzle, wherein the suction of the eductor pulls gas from the gas phase of the reaction mixture, mixes the gas with the circulated liquid, and returns the resulting mixture of liquid and gas back into the liquid phase of the reactor.

8. The process of claim 1, wherein a portion of the liquid phase is withdrawn from the reaction mixture and pumped through a spray nozzle, wherein the spray leaving the spray nozzle goes through the gas phase and absorbs some of the gas phase and returns to the reaction mixture.

9. The process of claim 1, wherein the reactor further comprises a draft tube to produce an internal recirculation inside the reactor.

10. The process of claim 1, wherein the halogenated methane with at least one chlorine atom is carbon tetrachloride.

11. The process of claim 1, wherein the alkene comprises ethylene and the halogenated alkene comprises vinyl chloride.

12. The process of claim 1, wherein the halogenated alkane is a chloroalkane, and the chloroalkane comprises 1,1,1,3-tetrachloropropane or 1,1,1,3,3-pentachloropropane.

13. The process of claim 1, wherein at least one catalyst comprises iron metal, copper metal, iron containing compound, copper containing compound, iron containing alloy, copper containing alloy, or combinations thereof.

14. The process of claim 13, wherein the at least one catalyst further comprises a trialkylphosphate, trialkylphosphite, or combinations thereof and wherein the trialkylphosphate, trialkylphosphite, or combinations thereof is complexed to Fe(II), Fe(III), Cu(I), Cu(II), or combinations thereof.

15. The process of claim 1, wherein the trialkylphosphate comprises triethylphosphate, tripropylphosphate, triisopropylphosphate, tributylphosphate, or combinations thereof; and wherein the trialkylphosphite comprises trimethylphosphite, triethylphosphite, tripropylphosphite, triisopropylphosphite, tributylphosphite, tri-tertbutylphosphite, or combinations thereof.

16. The process of claim 1, wherein the reaction mixture is maintained at a temperature from about 80° C. to about 140° C.; and the process is conducted at a pressure from about atmospheric pressure (~14.7 psi) to about 200 psi.

17. The process of claim 1, wherein the process is continuous.

18. The process of claim 1, wherein the weight % of the halogenated alkane is at least 50 weight % in the liquid phase of the reactor.

19. The process of claim 1, wherein the reaction is conducted in a series of stirred tank reactors.

20. The process of claim 1, wherein the ion exchange resin comprises a cation exchange resin.

21. The process of claim 17, wherein the phosphorous compound and halogenated methane comprising at least one chlorine atom are continuously added to the reactor.

22. The process of claim 1, wherein the at least one catalyst metal is part of a structured packing or un-structured packing.

* * * * *